(12) United States Patent
Yoshida et al.

(10) Patent No.: US 6,270,505 B1
(45) Date of Patent: Aug. 7, 2001

(54) ENDO-BAG WITH INFLATION-TYPE RECEIVING MOUTH AND INSTRUMENT FOR INSERTING ENDO-BAG

(75) Inventors: Osamu Yoshida, 38-3 Miyake-cho, Iwakura, Sakyo-ku, Kyoto-shi, Kyoto; Toshiro Terachi, 54 Kawara-cho, Shogoin, Sakyo-ku, Kyoto-shi, Kyoto; Ryuichiro Niizeki, Kyoto, all of (JP)

(73) Assignees: Osamu Yoshida; Toshiro Terachi, both of Kyoto; Japan Science and Technology Corporation, Saitama; J. Morita Manufacturing Corporation, Kyoto, all of (JP)

( * ) Notice: Subject to any disclaimer, the term of this patent is extended or adjusted under 35 U.S.C. 154(b) by 0 days.

(21) Appl. No.: 09/314,643

(22) Filed: May 19, 1999

(30) Foreign Application Priority Data

May 20, 1998 (JP) .................................................. 10-139014
Apr. 9, 1999 (JP) .................................................. 11-103111

(51) Int. Cl.[7] ..................................................... A61B 17/22
(52) U.S. Cl. ............................................................. 606/127
(58) Field of Search ..................................... 606/106, 110, 606/114, 127, 128

(56) References Cited

U.S. PATENT DOCUMENTS

| | | | | |
|---|---|---|---|---|
| 5,176,687 | * | 1/1993 | Hasson et al. | 606/114 |
| 5,215,521 | * | 6/1993 | Cochran et al. | 606/128 |
| 5,312,417 | * | 5/1994 | Wilk | 606/114 |
| 5,337,754 | * | 8/1994 | Heaven et al. | 606/114 |
| 5,853,374 | * | 12/1998 | Hart et al. | 606/114 |

* cited by examiner

*Primary Examiner*—Jeffrey A. Smith
*Assistant Examiner*—Eduardo C. Robert
(74) *Attorney, Agent, or Firm*—Koda & Androlia

(57) ABSTRACT

An endo-bag with an inflation-type receiving mouth comprising a flexible bag body having an organ receiving mouth provided with an inflation-type frame edge and an inserting portion for a surgical instrument such as forceps and laparoscope or the like. The inflation-type frame edge is provided with gores formed by three-dimensional tailoring and being so constructed as to be inflated and expanded to open said organ receiving mouth by pumping a fluid therein. The endo-bag can be easily and rapidly inflated and expanded to open the organ receiving mouth by pumping a fluid at low pressure and with small amount.

41 Claims, 39 Drawing Sheets

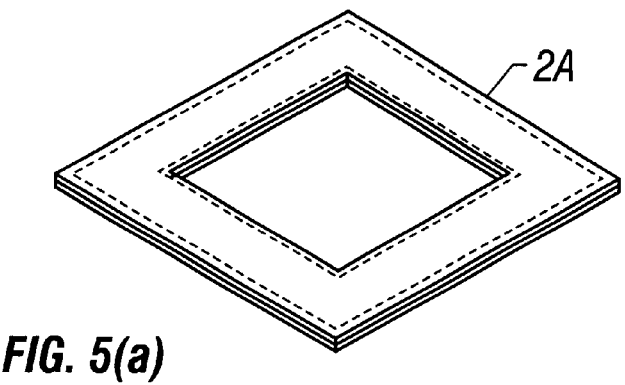
FIG. 5(a)
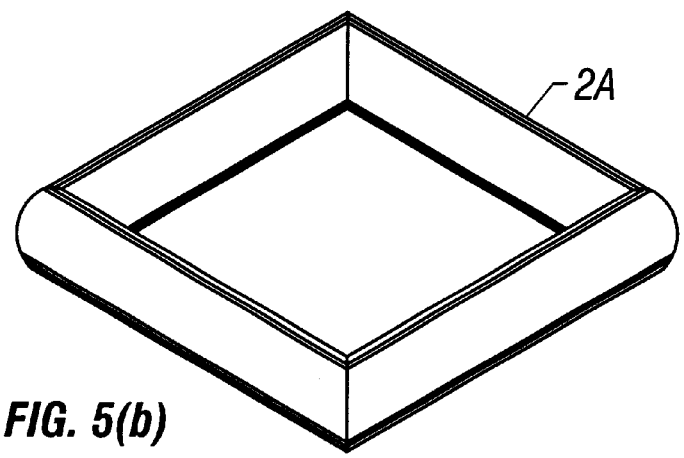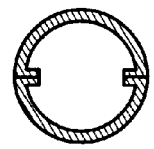
FIG. 5(b)
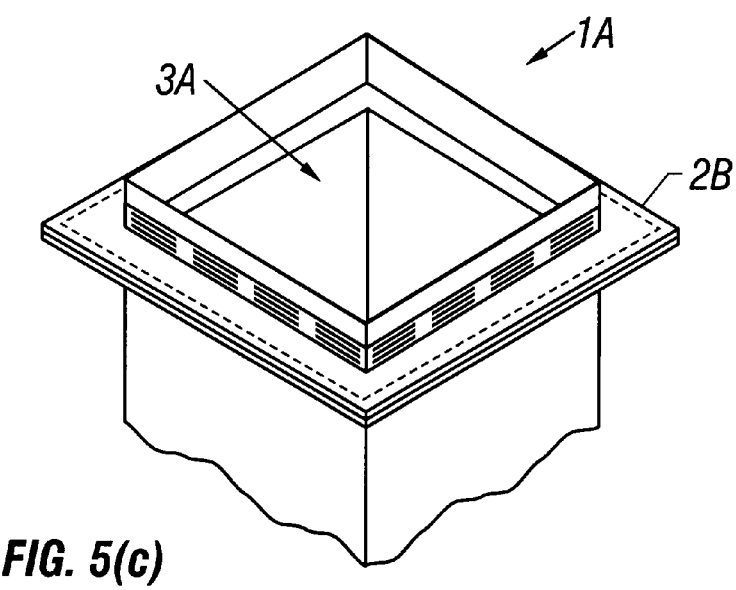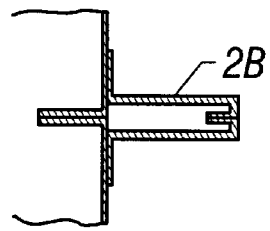
FIG. 5(c)

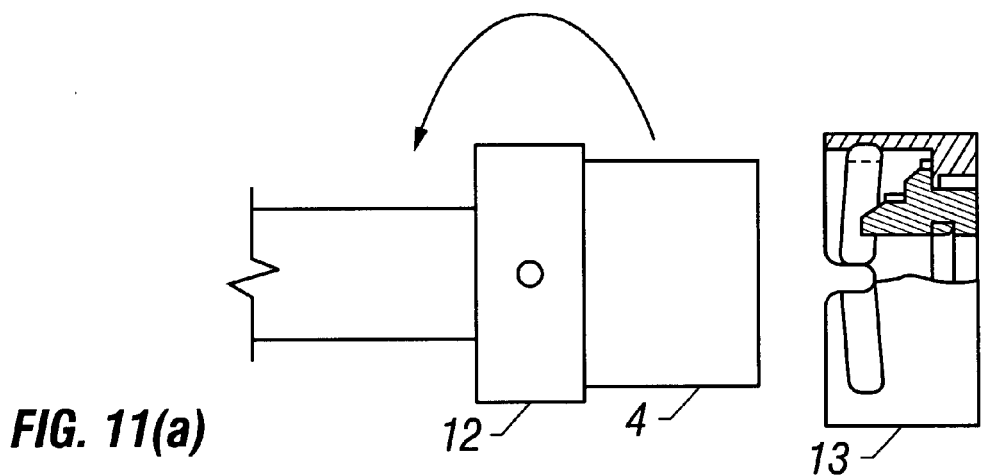
FIG. 11(a)
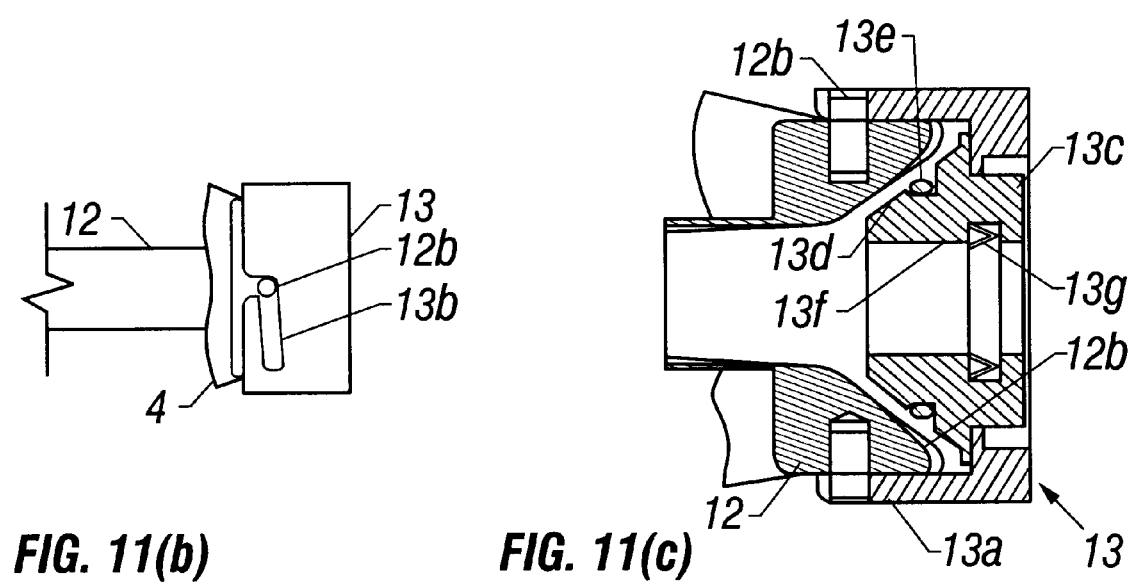
FIG. 11(b)   FIG. 11(c)
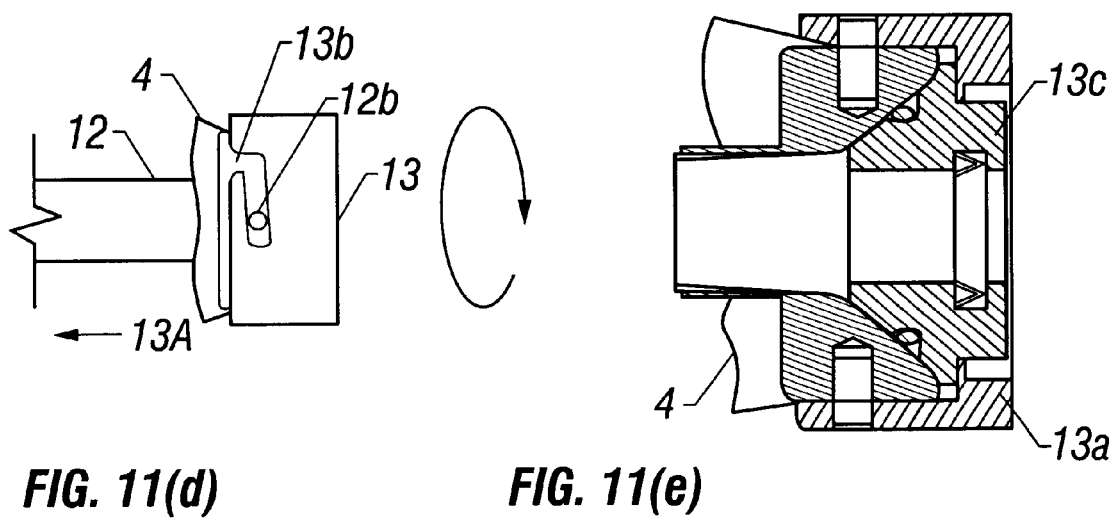
FIG. 11(d)   FIG. 11(e)

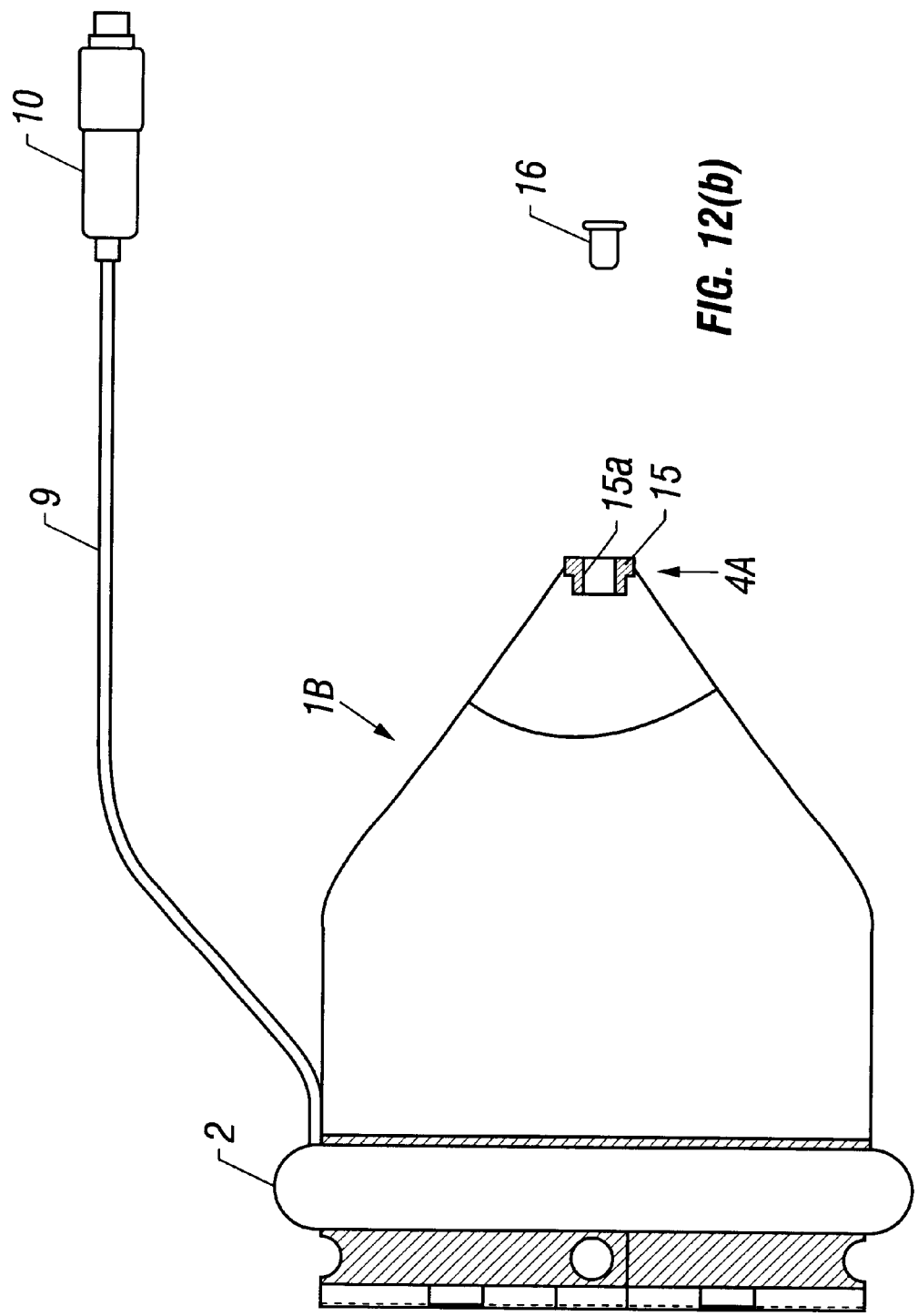

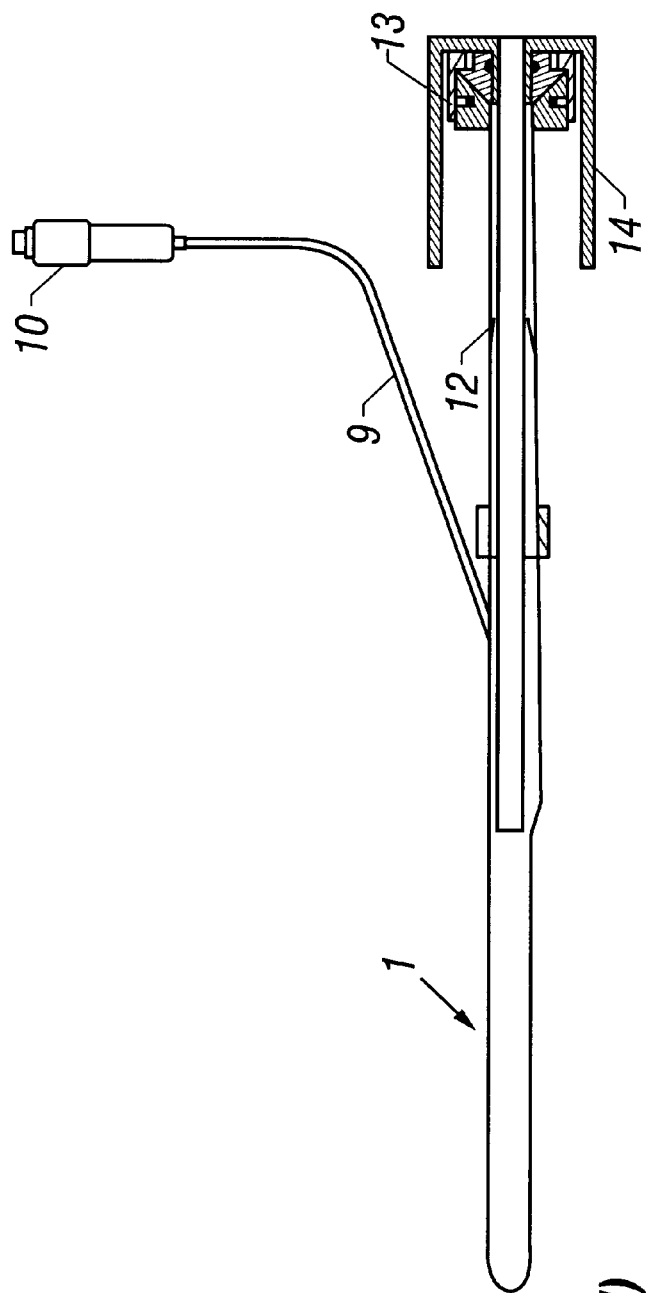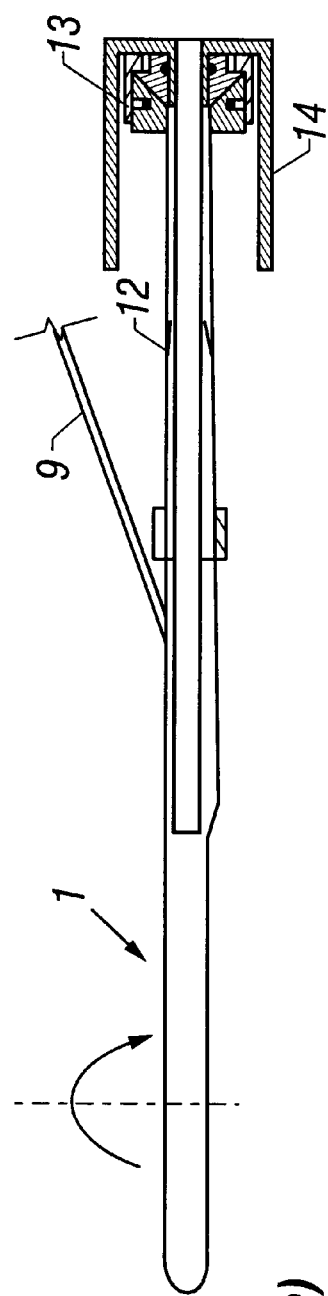
FIG. 16(d)
FIG. 16(e)

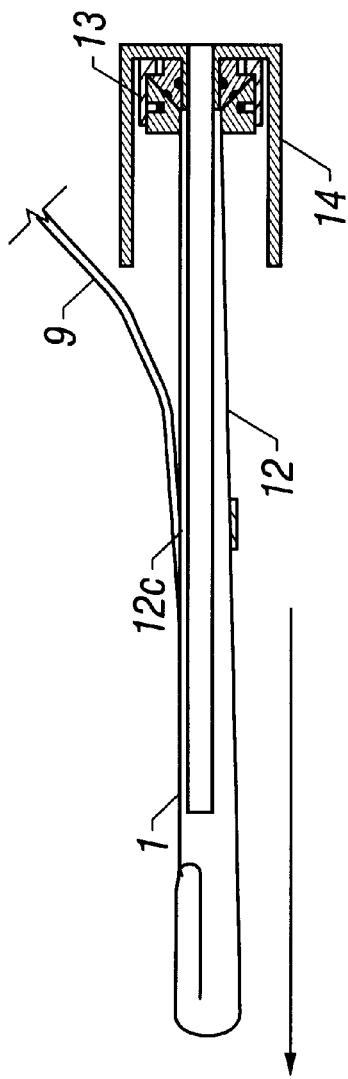
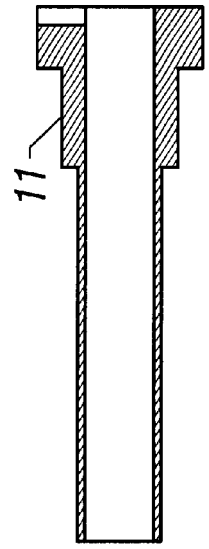
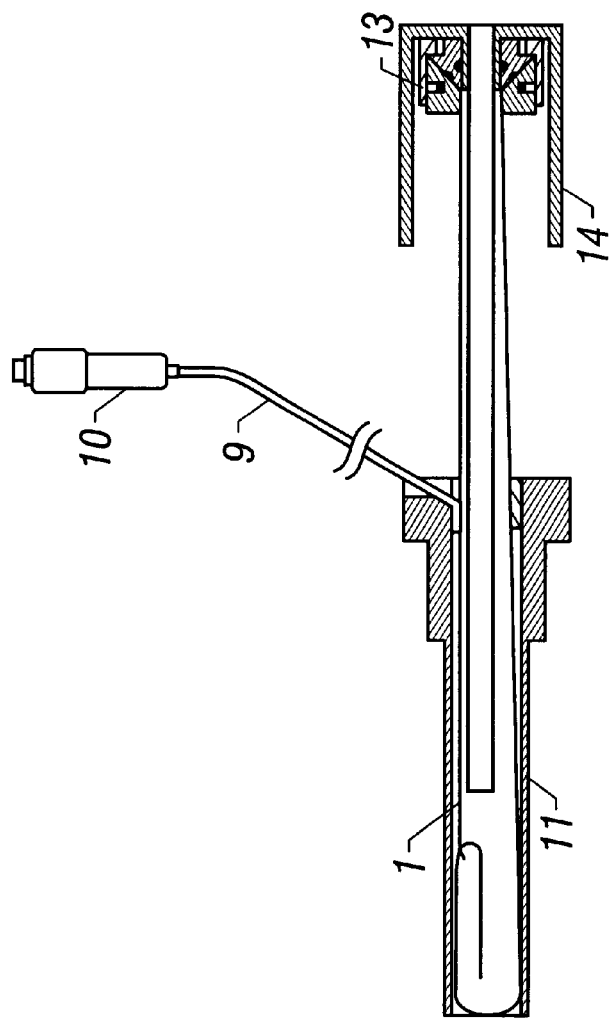
FIG. 17(f)
FIG. 17(g)

ENDO-BAG WITH INFLATION-TYPE RECEIVING MOUTH AND INSTRUMENT FOR INSERTING ENDO-BAG

BACKGROUND OF THE INVENTION

1. Field of the Invention

The present invention relates to an endo-bag to take in a removed organ as in an endoscopic surgery or an operation under an endoscopic examination and means for inserting the endo-bag into the abdominal cavity.

2. Description of the Prior Art

The endoscopic surgery is performed in the operation of the abdominal cavity and pectoral cavity. In this style of operation, the whole of the abdomen is not cut open. Instead, a minimum necessary part is cut open or holed, and through that opening are inserted a laparoscope and surgical instruments such as forceps and electric surgical knife with which a diseased organ is removed in the abdominal cavity under an endoscopic examination. This surgery is widely conducted lately, because a small abdominal opening does do for operations and helps quicken post-operation recovery and minimizes the creeping in of virus.

To prevent the operation from affecting the other parts, an endo-bag is used to take in a removed organ in the abdominal cavity. Then, the removed organ is cut in small pieces within the bag or put out of the cavity as it is removed. Since the diseased organ is taken in the bag immediately after surgery and all the subsequent treatment of the diseased organ is done within the bag, there is no possibility of the other parts of the body being affected even if the disease is a malignant tumor. This way, the endo-bag minimizes the adverse effect of operation on the patient.

In the meantime, the endoscopic operation is limited in degree of freedom of operation as compared with laparotomy because of the small trocar site, the limited visibility, ocellar observation of the laparoscope, and other factors. And the problem in using an endo-bag in the abdominal cavity is how the organ receiving mouth can be expanded and opened surely and quickly to take in the removed organ.

Different endo-bags addressing that question have been disclosed. The applicants of the present invention have also proposed an endo-bag in Japanese Patent Laid-open No. 9-173337 (unexamined).

FIG. 39 shows some examples of the prior art endo-bags.

An endo-bag 31 as shown in FIG. 39(a) has an elastic opening element 32 which springs open in the form of a ring when force is applied through an opening guide 34. The endo-bag 31, folded around the outer circumferencial surface of a guide inner cylinder 36, is housed inside an outer guide cylinder 35, with the opening element 32 stored in the opening guide 34. This endo-bag 31 is then inserted into the abdominal cavity by means of the outer guide cylinder 35, where the opening element 32 is caused to expand in the form of a ring by an opening means (not shown) so as to expand the bag 31 and to open the organ receiving mouth 33.

That method offered some advantages in that the endo-bag could be opened in a relatively simple mechanism. But since the opening element 32 having a certain rigidity and the opening guide 34 had to be used within the abdominal cavity almost with invisibility, it was necessary to take care so as not to harm the human internal organs and it was difficult to open the bag in an ideal state.

FIGS. 39(b) and (c) show endo-bags which are opened not by using a rigid element but by providing a hollow space in the whole or part of the bag into which air or the like is pumped to open the bag.

In the endo-bag 41 shown in FIG. 39(b), an organ receiving mouth 43 is provided with an inflation-type frame edge 42 formed of a ring-formed hollow space. In this inflation-type frame edge 42, a tube 45 is led out through a surgical instrument inserting portion 44. Into this tube 45, air or the like is pumped to inflate the inflation-type frame edge 42 which then opens the organ receiving mouth 43.

In the endo-bag 51 in FIG. 39(c), the whole bag is an inflation-type flabby cylinder 52 in shape. In this, air or the like is led from the surgical instrument inserting portion 54 through the tube 55 to inflate the inflation-type flabby cylinder 52 and then to open an organ receiving mouth 53. The reference numerals 46 and 56 indicate additionally provided surgical instrument inserting portions through which the forceps and the laparoscope are passed so as to permit treatment within the bag.

Those endo-bags were excellent with regard to safety, because the bag itself was formed of such materials as polyethylene sheet that were not harmful to the human body.

But the problem with those endo-bags were that a considerable amount of air was required for the bag to take shape and open. The pressure of air, too, had to be raised to a considerable level. Otherwise, the bag would not open in an ideal state and could deform under the slightest stress. If the inflation-type frame edge or the inflation-type flabby cylinder should burst out, the leaked air could push up the pressure in the abdominal cavity and contaminate the abdominal cavity. For that reason, there had been a call for development of an endo-bag that could open in an ideal state with a less amount of air.

Also, a variety of opening systems including those aforesaid examples had been disclosed, but there had been found no systems which were completed on the basis of consideration of opened form and three-dimensional tailoring. That is because such materials as polyethylene sheet or urethane sheet were selected for the endo-bag on account of foldability, strength, harmlessness to humans, transparency and others. And the pliability of those materials led to a belief that it was natural that the opened form should be round or the like.

SUMMARY OF THE INVENTION

In view of those problems with the prior art endo-bags, the present invention has been provided. Accordingly, and it is a primary object of the present invention to provide an endo-bag for endoscopic operation which can be easily and rapidly opened without difficulty with a low pressure and a small quantity of fluid and that will not deform easily and a means to insert the endo-bag.

The present invention discloses endo-bags which comprise an inflation-type frame edge provided with three-dimensionally tailored gores and an organ receiving mouth that will be opened in not circular but polygonal form by the inflation-type frame edge.

As mentioned above, the present invention is based on the idea of the three-dimensional tailoring of the material for the inflation-type frame edge and its opened form to which nobody had paid attention. That is, the material is three-dimensionally tailored so as to make it easy to inflate the material. At the same time, what form to take is not left to the material itself but manipulated. After much trial and error, it was found that three-dimensional tailoring and polygonal, and not circular, form could open the endo-bag with a lower pressure and a small quantity of fluid. Furthermore, the bag when opened and expanded was resistant to deformation. Those ideas are incorporated into the present invention.

It is also noted that the endo-bag of the present invention is for use in endoscopic operation. In an endoscopic operation, the bag is inserted into the abdominal cavity or thoracic cavity where a removed organ is put in the bag and can be given necessary treatment while observing the organ in the bag by an endscope. It is also possible to bring out of the trocar puncture the bag containing the organ as it is removed.

According to such an airtight endo-bag, when the opening such as an organ receiving mouth of an endo-bag is sealed appropriately, the organ contained in the endo-bag can be treated while the inside of the endo-bag is inflated by pumping air therein. Therefore, good visibility of endscope can be achieved and such an endo-bag is suitable for endoscopic surgery.

The endo-bag as defined in the present invention is so designed that an inserting portion for surgical instruments such as forceps and laparoscope is formed in a flexible bag body having an organ receiving mouth provided with an inflation-type frame edge. The inflation-type frame edge is provided with gores formed by three-dimensional tailoring into which a fluid is pumped to open the organ receiving mouth.

The reason that gores are created by three-dimensional tailoring is this. When an inflation-type frame edge made with a pliable material such as urethane sheet inflates and takes a three-dimensional form, the sheet could stretch unevenly. The gore created by three-dimensional tailoring eliminates such an uneven stretching.

It is ideal that the sheet should be tailored in a perfectly three-dimensional shape in which the bag is inflated when the fluid is pumped in. Then no elastic force of the sheet from stretching will occur or prevent the fluid from flowing in until after that three-dimensional shape is set up. That is, the three-dimensional shape could be established with the organ receiving mouth opening with the least pressure. But it is technically too difficult to make such a bag. In practice, a good way is to cut a plane sheet into pieces with which a three-dimensional shape such as slack and gore can be created. That way, it is possible to inflate the inflation-type frame edge in a specific form and to open the organ receiving mouth. Further the gores are designed so that the bag can be folded compact.

The opened form is not limited to polygonal, but may be circular, elliptic or the like.

The endo-bag as defined in the present invention is distinguished by its opened form. This bag has a flexible bag body with an organ receiving mouth provided with an inflation-type frame edge. This bag body has an inserting portion for surgical instruments such as a forceps, a laparoscope and the like. The inflation-type frame edge expands in a polygonal shape to open the organ receiving mouth when a fluid is pumped in.

The advantage of the polygonal shape is that when the frame edge is further enlarged after having expanded to a specific shape, the surface will stretch relatively uniformly. That is, a lower pressure will do. Since the shape is angular, in addition, the shape is resistant to deformation by external force.

The endo-bag as defined in the present invention is so designed that an inserting portion for a surgical instrument such as a forceps and a laparoscope, or the like is formed in a flexible bag body having an organ receiving mouth provided with an inflation-type frame edge. According to such a bag body, the inflation-type frame edge is so constructed as to be formed in a circular or polygonal shape made of series of plural segments expanded by pumping a fluid to open the organ receiving mouth.

According to such a bag body, the inflation-type frame edge is divided into plural segments and a tube for pumping a fluid is provided for each segment independently or commonly. Therefore, the bag becomes easy to be inflated uniformly.

In the endo-bag as defined in claim 4, the aforesaid inflation-type frame edge is provided with gores at appropriate intervals around the outer circumference so as to form corners of the polygon.

The expression "gore" as used herein is especially defined as follows: If air is pumped in between two sheets that are bonded to each other on the surrounding edge, a cylindrical shape will be produced. If one sheet is a little longer than the other and the edges of the two sheets are bonded with the longer piece doubled to adjust its length to that of the shorter one, then the doubled part will bulge out when air is pumped in, forming corners. And a bent cylinder will be formed as a whole. That doubled area is referred to as "gore".

An endo-bag is formed of sheet material that way with gores created at appropriate intervals around the outer circumference by bonding additional sheets at the mouth of the bag to produce an inflation-type hollow frame edge. This inflation-type frame edge will readily form a polygon when inflated. Furthermore, the bag can be made small when folded.

The endo-bag as defined in the present invention has the joints of the aforesaid gores inside the aforesaid corners.

The joints bonded as by thermocompression technique are slightly harder than the other part and do not stick out of the bag. That is, there is no possibility that the joints will damage human tissues in the abdominal or thoracic cavity. In addition, the joints serve as reinforcing ribs provided inside the corners, erecting the polygonal corners and improving the stability of the whole shape.

As used herein, the term "inside" denotes the inner side in which the fluid is pumped to inflate the inflation-type frame edge.

In the endo-bag as defined in the present invention, as the polygon is triangular, quadrangular or pentagonal, it is very useful for practical use.

In the endo-bag as defined in the present invention, it is so arranged that the aforesaid inflation-type frame edge inflates almost uniformly over the surface when a fluid is pumped in, so that it can be inflated with less pressure.

In the trial and error experiments, the inventors found that because of the shape, the circular inflation-type frame edge will increase in inside diameter and outside diameter in addition to sectional expansion as it is inflated. In other words, the inner circumference and the outer circumference will grow. It should also be noted that the inner diameter and the outer diameter are not equal in degree of inflation. In the polygonal inflation-type frame edge, on the other hand, there takes place no surface stretching other than sectional inflation which does not differ from area to area in degree of stretching.

From those observations, it was concluded that if it were so designed that the surface inflated evenly, a low pressure would do to expand the frame edge.

The endo-bag as defined in the present invention has the gores in the form of bellows, which constitute the corners of the polygon.

Bellows are formed of a number of small gores, which produce the same results as a full-size gore.

In the endo-bag as defined in the present invention, the aforesaid frame edge comprises with a plurality of inflation-type circular cylindrical bodies communicating with each other.

In a quadrangle, for example, it is so constituted that four circular cylindrical bodies communicate with each other through respective fluid passages that are short and small in diameter. And when a quadrangle is set up, the circular cylinders will stretch uniformly inside and outside, with the frame edge inflating to a specific shape with a lower pressure.

The endo-bag as defined in the present invention has a polygonal inflation-type frame edge with circular arc corners. The same effect of the above-mentioned gores can be obtained.

In the endo-bag as defined in the present invention, the aforesaid inflation-type frame edge is formed of a low-stretchable sheet.

Because the sheet is low in stretchability, the frame edge, once inflated, maintains its shape firmly. That is, an ideal shape can be held without much additional pressure applied. Furthermore, the frame edge does not expand and reserve an excessive amount of fluid, and therefore if the frame edge should burst out in the abdominal cavity, the amount of fluid leaking therein will be kept to a minimum without causing much influence of the pressure.

The endo-bag as defined in the present invention is provided with a closing margin around the organ receiving mouth. The closing margin has a plurality of through holes through which a closing string is passed.

The closing string can shut the organ receiving mouth of the bag.

In the endo-bag as defined in the present invention, the aforesaid closing margin is provided with catching holes.

By those catching holes, it is possible to catch and hold the bag easily and securely with a forceps or the like while observing the abdominal cavity under the laparoscope. Furthermore, there is no fear that the bag will be damaged because the catching holes are located away from the bag body.

The endo-bag as defined in the present invention is provided with a knotless and endless closing string. The closing string, which is endless without knots, can move smoothly through the holes and will not hinder the bag from closing.

In the endo-bag as defined in the present invention, the aforesaid inserting portion for surgical instruments is provided on the opposite side of the bag from the organ receiving mouth.

That arrangement facilitates manipulating surgical instruments such as a forceps in taking in an organ through the organ receiving mouth in usual operation.

The endo-bag as defined in the present invention is so constructed that the surrounding wall forming the bag is provided with a plurality of inflation-type rib frames communicating with the aforesaid inflation-type frame edge. The plurality of inflation-type rib frames run the organ receiving mouth toward the inserting portion for surgical instruments.

In that arrangement, the organ receiving mouth opens at the polygonal inflation-type frame edge. As the frame edge opens, the whole bag flares out in a form just like a megaphone of which length is small (with sharp inclination). That is, at the same time that the organ receiving mouth opens, the bag stands ready to take in the organ conveniently.

In the endo-bag as defined in the present invention, the aforesaid bag is formed of a strong and pliable urethane or polyethylene sheet at 50 to 80 micron in thickness.

This type of bag can be inserted in a folded state into the abdominal cavity through a trocar and put through the trocar puncture in an endoscopic operation. The bag of that kind is convenient for endoscopic operations.

In the endo-bag as defined in the present invention, the aforesaid bag is made with a transparent or semitransparent urethane sheet or polyethylene sheet.

This bag permits observing inside and does not limit the visual range of the laparoscope so much, therefore facilitates instrument manipulation.

In the endo-bag as defined in the present invention, the bag part of the bag body is double constructed. The bag part, herein, indicates a part wherein an organ is contained and treated, except for the organ receiving mouth with an inflation-type frame edge and the inserting portion for surgical instruments. As the bag part is double constructed, the endo-bag is hard to be broken and has high safety.

Even if such an endo-bag is broken while the removed organ therein is treated with a forceps and so on, malignant tumor or the like is prevented from leaking out of the bag because of the double constructed bag part.

In the endo-bag as defined in the present invention, clean air, carbonic acid gas or sterilized distilled water is pumped in as a fluid.

As a shape can be reached and maintained with a less amount of fluid under a lower pressure, the broad option of fluids widens the application possibility of the bag.

In the endo-bag as defined in the present invention, the aforesaid portion for inserting surgical instruments is provided with an instrument receiving member with an insertion hole which conforms to the shape of a surgical instrument to be inserted and a sealing plug to seal the insertion hole air-tight.

The insertion hole minimizes the gap between the hole and the surgical instrument, thereby reducing possible effects from outside. When no instrument is used, the insertion hole can be closed with the sealing plug. Further, carbonic acid gas inflating the bag and the body fluid in the bag are prevented from leaking out.

Accordingly, it is an secondary object of the present invention to provide an instrument for receiving endo-bag so as to improve the operation of the bag.

The present invention discloses means for inserting the endo-bags as mentioned above into the abdominal or thoracic cavity. The aforesaid means permit insertion of those bags without fear of damaging the bag.

To be specific, the endo-bag inserting means as defined in the present invention comprises a guide cylinder to guide the endo-bags as described above, folded, into the abdominal cavity and a push shaft to insert those endo-bags, facilitating insertion of the endo-bag.

The endo-bag inserting means as defined in the present invention comprises a guide cylinder to guide the endo-bags as mentioned above, folded, into the abdominal cavity and a push shaft to insert those endo-bags, with the guide cylinder provided with a seal mechanism to seal one end of the instrument inserting portion in the aforesaid endo-bag and with the aforesaid push shaft provided with an insertion hole. Through this insertion hole, it is possible to send in surgical instruments such as a forceps and a laparoscope in an airtight state after the endo-bag is inserted.

Very effective in sealing the hole, that arrangement can minimize effects on the abdominal cavity of the outside air and others and also can prevent the substances contained in the bag and air to inflate the bag from leaking out.

The endo-bag inserting means as defined in the present invention comprises a guide cylinder to guide the endo-bags, folded, into the abdominal cavity and a push shaft to insert those endo-bags, with the aforesaid push shaft provided with a fitting hole. The fitting hole corresponds with the shape of the aforesaid instrument receiving member to be passed when the hole is fit into the shape of the member.

As long as the instrument receiving member is not fit into the corresponding hole of the push shaft, the member is held on the end face of the push shaft. Through that insertion hole, the surgical instrument can be passed for preparation work. After work, the surgical instrument can be inserted into the abdominal cavity with the insertion hole closed with the sealing plug. This arrangement is suitable for inserting the endo-bag and also excellent in sealing effect. Thus, it is possible to minimize the effects on the abdominal cavity from the outside air and the like and to prevent the substances placed in the bag from leaking out.

BRIEF DESCRIPTION OF THE DRAWINGS

FIGS. 5(a)~5(c) show another ideal method to form a polygonal shape.

FIG. 8 explains another gore parts of the inflation-type frame edge of the endo-bag of the present invention.

FIG. 10 shows one embodiment of the parts comprising the instrument for inserting endo-bag of the present invention.

FIG. 11 explains the seal mechanism of the instrument for inserting endo-bag.

FIG. 11(a) shows when the inserting portion of the surgical instrument of the endo-bag is passed through the push shaft, FIG. 11(b) shows the state before the end of the inserting portion is fixed with the cap, FIG. 11(c) shows its section, FIG. 11(d) shows the state after the inserting portion is fixed, and FIG. 11(e) shows its section.

FIG. 12 shows another embodiment of the endo-bag of the present invention.

FIG. 12(a) is an external view showing a partial section and

FIG. 12(b) is a front view of the sealing plug.

FIG. 16(d) shows the state when the endo-bag is folded, and

FIG. 16(e) shows when the tipping end of the folded endo-bag is bent.

FIG. 17(f) shows when the folded endo-bag is contained in the guide cylinder, and FIG. 17(g) shows setting condition of the endo-bag before it is used.

FIG. 28 shows the parts comprising another embodiment of the surgical instrument for inserting the endo-bag of the present invention.

FIG. 29(*b*) is a vertical sectional view of the push shaft having a pipe guide, and FIG. 29(*c*) is a sectional view of the cap for folding.

FIG. 30(*b*) is a vertical sectional view of the forceps guide.

FIG. 38(*k*) shows when the organ receiving mouth is closed by pulling the closing string after the removed organ is taken in.

DETAILED DESCRIPTION OF THE INVENTION

With reference to the accompanying drawings, an endo-bag with inflation-type receiving mouth and a surgical instrument for inserting the endo-bag will be described hereinafter.

Now, the construction of endo-bag will be explained.

Figure 1:
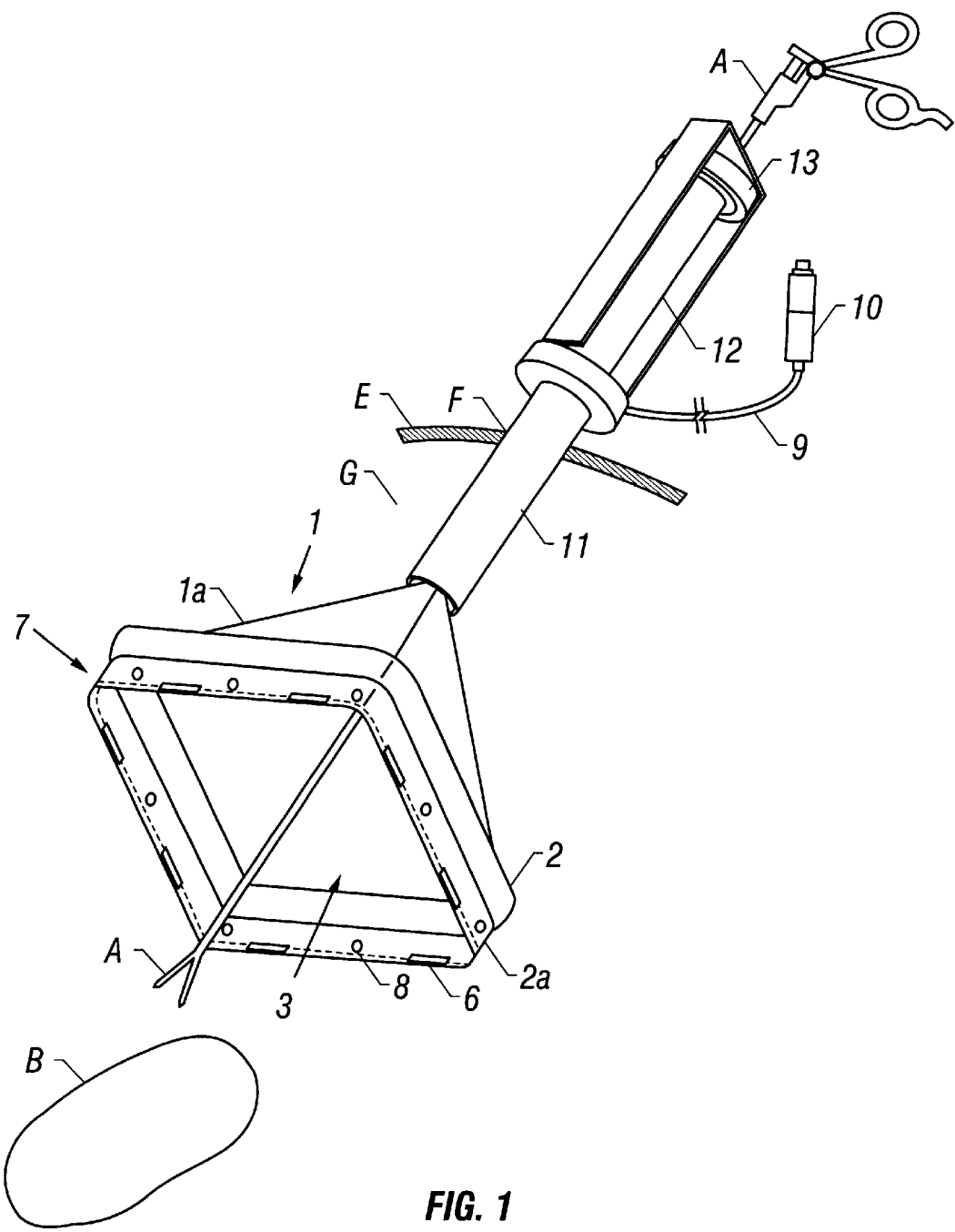
FIG. 1 is a diagrammatic perspective view of one embodiment of the inflated endo-bag according to the present invention.
Figure 2:
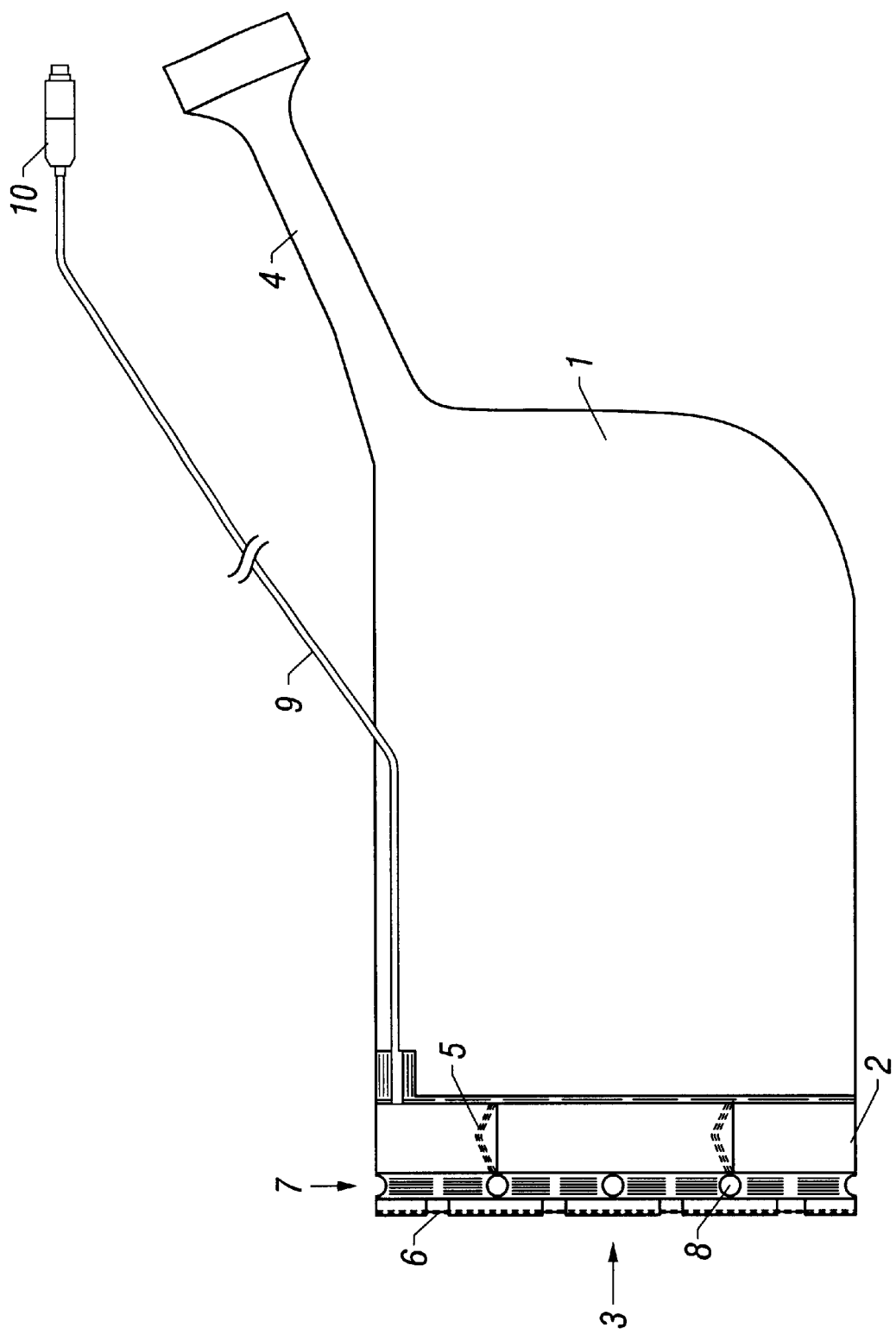
FIG. 2 is an external view of the one embodiment of the endo-bag according to the present invention.
Figure 3A:
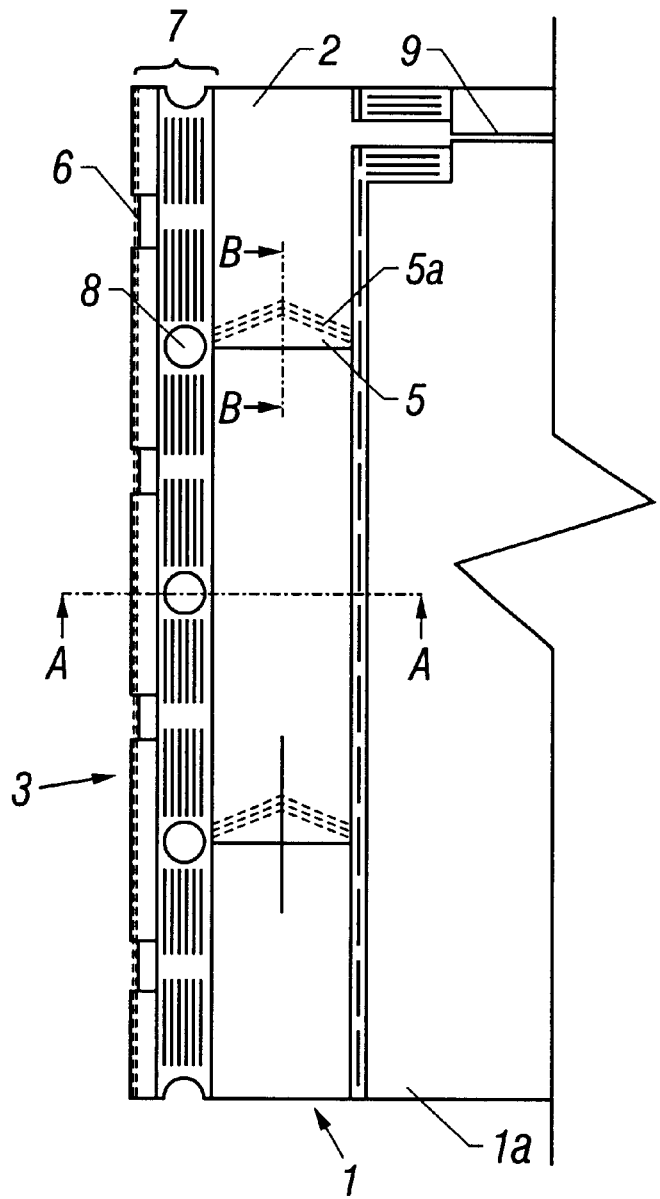
FIG. 3(a) is a partial detailed view around an organ receiving mouth for of the endo-bag of the present invention and FIG. 3(b) is a sectional view taken along the line A—A.
Figure 3B:
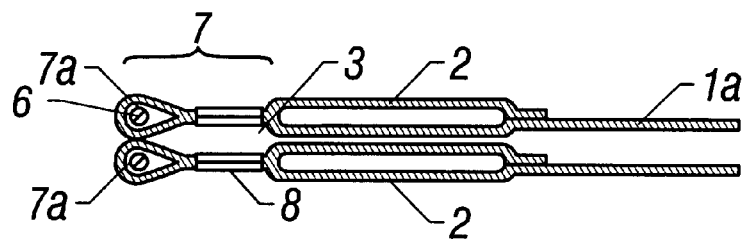

FIG. 1 is a diagrammatic perspective view of one embodiment of the inflated endo-bag according to the present invention. FIG. 2 is an external view of the one embodiment of the endo-bag according to the present invention. FIG. 3(*a*) is a partial detailed view around an organ receiving mouth of the endo-bag of the present invention and FIG. 3(*b*) is a sectional view taken along the line A—A.

In the figures, the reference numeral 1 indicates an endo-bag, 2 is an inflation-type frame edge, 3 is an organ receiving mouth, 4 is an inserting portion for a surgical instrument, 5 is a gore, 6 is a closing string, 7 is a closing margin, 8 is a catching hole, 9 is a tube, and 10 is a check valve.

Further, the numeral 11 is a guide cylinder and 12 is a push shaft, both of which comprise an instrument for inserting endo-bag. They are incorporated into a trocar site F instead of a trocar (not shown) which is usually provided for the trocar site F provided for a patient's body E, and used for inserting the endo-bag 1 into an abdominal cavity G. The reference character A indicates a forceps, and B indicates a removed organ.

The endo-bag 1 is inserted into the abdominal cavity G, a folded endo-bag 1 is exposed from the inside of the guide cylinder 11, and a syringe (not shown) is inserted in a check valve 10. When fluid such as such as a clean air is pumped, the fluid runs to the inflation-type frame edge 2 through the tube 9. Because the inflation-type frame edge 2 has gores 5 at its outer circumference, corners 2*a* are formed at first with low pressure and small amount of fluid. Accordingly, the frame edge 2 is formed polygonal, quadrangular this time, easily and certainly because of further pumped fluid.

As mentioned above, the present invention is characterized in that the opening shape of the organ receiving mouth 3 is intentionally made polygonal. As a result, such a mouth can be opened easily and certainly with lower pressure and smaller amount of fluid comparing to the circular shaped frame edge. Further, it is resistant to deformation by external force and appropriate for the endoscopic surgery. Furthermore, because the shape of the organ receiving mouth 3 is polygonal having straight sides, the bottom side has good stability and it is hard to hinder the removed organ B from taking therein comparing to the prior art having a circular opening shape.

A fluid such as clean air, carbonic acid gas or sterilized distilled water which has less adverse effect on the patient even if the fluid is leaked in the abdominal cavity can be appropriately selected and its selection range is broad. When the fluid is leaked out because of the breakage of the bag, the amount is small and adverse effect on the patient can be restrained at minimum. Comparing to the prior arts, because the endo-bag 1 is expanded and opened along the abdominal wall, a large opening can be produced even in the narrow space of the abdominal cavity and the removed organ B can be easily taken in.

The organ receiving mouth 3 is opened quadrangular, accordingly, it is set as shown in the figure by inserting the forceps A from an insertion hole (not shown) provided for the push shaft 12. Then the removed organ B can be easily taken in the endo-bag 1 by catching the removed organ B by means of the forceps A.

The endo-bag 1 is transparent or semi-transparent, strong and flexible urethane sheet or polyetylene sheet with 50~80 micron thickness. It can be contained in the guide cylinder 11 when folded and the folded bag 1 is inserted in the abdominal cavity by means of the push shaft 12.

Several kinds of material and thickness of the sheet material for the endo-bag 1 can be selected if it satisfies following condition: it doesn't have adverse effect on the abdominal cavity; oozed constituent of the contained removed organ B isn't leaked out; it has enough strength so as not to be broken when the forceps operation and cutting operation are executed therein; it has chemical stability, and it can be folded so as to pass through the trocar.

When the sheet material of the endo-bag 1 is transparent or semi-transparent, the visual field of the laparoscope, which is an only eye in case of endoscopic surgery, can't be hindered. Further, the contained removed organ B can be seen from outside of the bag 1 and the organ around the removed B organ can be also seen from the bag 1 by means of a laparoscope. Therefore, such a sheet material has high stability and is appropriate for the endoscopic surgery because operation can be done while confirming so as not to damage the organ outside of the bag 1 when the organ B contained in the bag 1 is treated with the forceps A.

The inflation-type frame edge 2 is provided around the organ receiving mouth 3 and made of the same material as the bag 1 or the material having particular pliability as mentioned after. Because of productive reason, it is usually made such that a band-like sheet material is piled and adhered on the outer circumference of the main body of the bag 1. The present invention is characterized in that the gore 5 is provided for the sheet material to be piled and adhered on the outer circumference. The construction and function thereof will be described after.

The closing margin 7 is provided for closing the organ receiving mouth 3 after the removed organ B is taken in the endo-bag 1 and the inflation-type frame edge 2 is shrunk. The edge of the closing margin 7 is provided with plural through holes 7a with the closing string 6 passing therethrough. When the closing string 6 is pulled up by catching with the forceps A, the organ receiving mouth 3 can be closed.

Because the closed string 6 has no knot or end, the mouth 3 can be closed smoothly without being caught in the through holes 7a when the string 6 is pulled up.

The catching holes 8 are appropriately provided for the attached portion of the closing margin 7 and they work as a hold for catching the endo-bag 1 by means of the forceps A. The catching holes 8 are formed as a hole so that they are caught in the picking part of the handgrip of the forceps A, therefore catching can be made easy and it makes hard to be removed. Further, the attached portion has higher strength than the other sheet material and isn't damaged easily. Furthermore, the holes 8 are provided apart from the bag portion 1a of the organ receiving portion, so that they don't cause leakage of the contained material even if the attached portion is damaged, thereby realizing high stability.

The check valve 10 is constructed so as to pass through the fluid when the fluid pumping means such as a syringe is inserted and to prevent the fluid from passing when the fluid pumping means is removed.

It is convenient because the fluid can be pumped or drawn only when the pumping means is inserted and the fluid filled in the tube 9 and the inflation-type frame edge 2 isn't drawn.

Next, the gores and the polygonal shape, which are the characteristics of the present invention, will be described hereinafter.

FIGS. 4(a)~4(d) is a diagrammatic explanatory view showing the procedure wherein a fluid is pumped in the inflation-type frame edge and the gores form the corner part. FIG. 4 shows a sectional view along the line B—B of the gore 5 shown in FIG. 3. According to FIG. 4, the section of the gore 5 forms the corner 2a at first accompanied with pumping of the fluid and further forms a fixed shape afterwards.

Figure 4A:
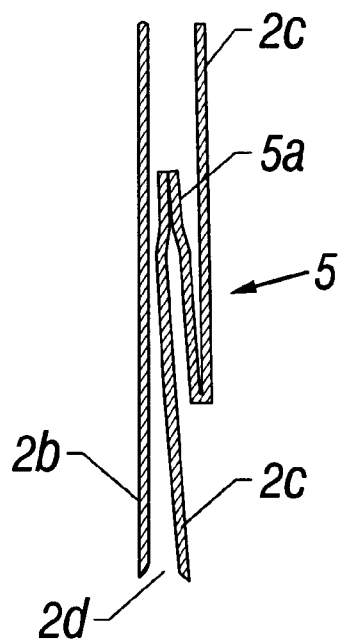
FIGS. 4(a)~4(d) is a diagrammatic explanatory view showing the procedure wherein a fluid is pumped in the inflation-type frame edge and the gores form the corner part.

FIG. 4(a) shows a sectional view of the gore 5 while a fluid isn't pumped. In this figure, a fixed space is shown in the inflation-type frame edge 2 for the purpose of understanding, however, actually the frame edge 2 is flat when a fluid isn't pumped at all.

As shown from the figure, an outside part 2c is made longer as the piled length of the gore 5 comparing to an inner part 2b of the inflation-type frame edge 2 when inflated. The shape of the folded and piled part of the gore 5 is triangular as shown in FIG. 3, that is the folded and piled amount is large at the center of the width of the frame edge 2 and it becomes smaller toward the direction of both ends. It is because that the gore 5 is formed by three-dimensional tailoring so as to be easily inflated into circular as the section of the inflated frame edge 2 becomes circular on account of the flexibility of the sheet material of the frame edge 2.

The reference numeral 2d indicates the inside of the inflation-type frame edge 2 and to which a fluid is pumped. The numeral 5a (see also FIG. 3) indicates a joint which is formed when a sheet material is three-dimensionally tailored and the edges are attached. The sheet material such as a urethane is bonded as by thermocompression technique so that the joint 5a becomes thicker and harder than the other part of the sheet material and has a constructional rigidity.

Figure 4B:
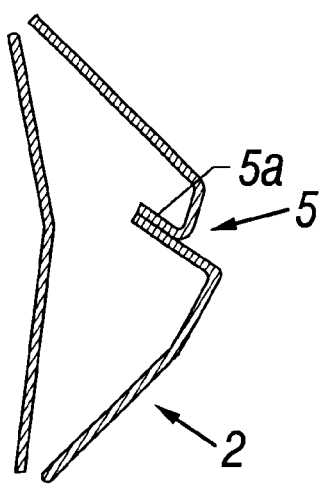

FIG. 4(b) shows immediately after a fluid is pumped. The gore 5 is folded inside so as to include the joint 5a in the inside 2d. Therefore, the gore 5 is designed to have space enough to easily induct fluid to inflate. Accordingly, the gore 5 is projected at first when fluid is pumped into the frame edge 2.

Figure 4C:
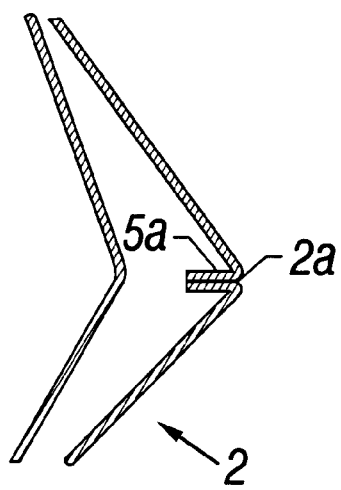

FIG. 4(c) shows the state when a fluid is further pumped. In this state, the corners 2a are already formed before the whole shape is established, then the whole shape becomes to be established along the corners 2a.

Figure 4D:
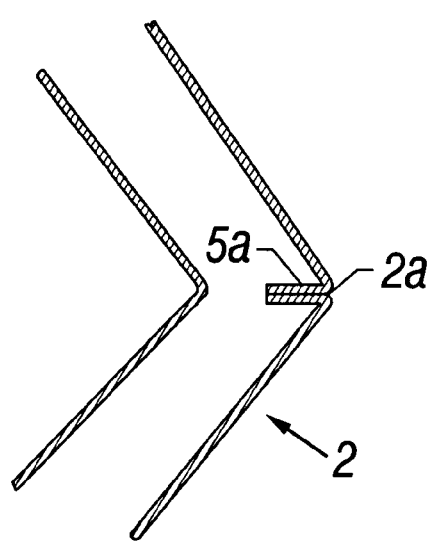

FIG. 4(d) shows the state when the whole shape is almost established. In this state, the corners are formed inside of the corners 2a in such a manner that the corners 2a leads forming of the inside corners, then the whole shape becomes polygonal.

Accordingly, the polygonal inflation-type frame edge 2 can be easily formed with a sheet material having gores 5. As shown in FIG. 4(d), the joints 5a are formed inside so that they don't damage the abdominal cavity. Further, as the joints 5a have some rigidity, they serve as reinforcing ribs provided inside the corners 2a, improving the stability of the corners 2a and being resistant to deformation by external force. The joints which are margins inevitably formed in production are ingeniously utilized as a part of construction.

In the above-mentioned explanation, gores are used to form a polygonal shape, however, the method wherein a pliable sheet material is bonded and a polygonal shape is formed by pumping a fluid isn't limited.

FIGS. 5(a)~5(c) show another ideal method to form a polygonal shape.

FIGS. 5(a) and 5(b) show one embodiment. FIG. 5(a) shows the state when a sheet material is cut and bonded, FIG. 5(b) shows when the bonded sheet material is inflated. In these figures, quadrangular shape is shown as one example. Sectional view is shown beside each figure to help understanding.

A sheet material is cut into window frame shape formed by a large and a small concentric squares and the edge thereof is bonded. The figures show the jointed margin becomes inside. Actually such a bonding is difficult, however, the figures show an idea to explain the advantage comparing to the method when the margin is set outside.

When a fluid is pumped inside of such bonded inflation-type frame edge 2A, the frame is inflated as shown in FIG. 5(b) and becomes quadrangular.

FIG. 5(c) shows one embodiment of an endo-bag 1A according to the method for forming polygonal shape.

The figure shows the endo-bag 1A with the organ receiving mouth 3A opened. The endo-bag 1A is provided with an inflation-type frame edge 2B which is formed according to the above-mentioned polygonal frame forming method around the organ receiving mouth 3A in such a manner that the edge 2B is projected like a brim. The edge 2B is projected inwardly as well as outwardly.

When a fluid is pumped to the inflation-type frame edge 2B, the edge 2B becomes polygonal with lower pressure like the edge 2, 2A as mentioned above, then the receiving mouth 3A is expanded and opened polygonally.

The polygonal shape to achieve the effects of the present invention isn't limited to quadrangle as mentioned above. FIGS. 6(a)~6(l) show various polygonal shapes.

FIGS. 6(a)–6(d) shows triangle, quadrangle, pentagon and hexagon. Each figure has the same effect. More angles can be made theoretically, however, it is limited to hexagon and quadrangle is easiest to be used.

Figure 6A:
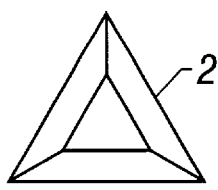
FIGS. 6(a)~6(l) show various polygonal shapes of the inflation-type frame edge.
Figure 6B:
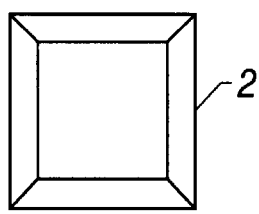
Figure 6C:
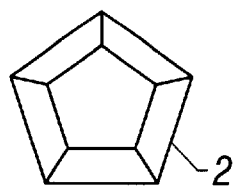
Figure 6D:
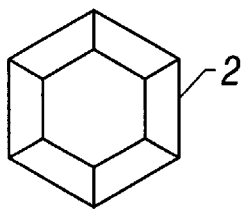
Figure 6E:
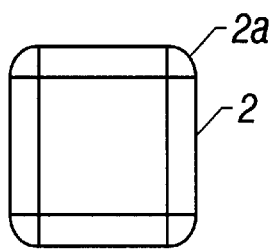
Figure 6F:
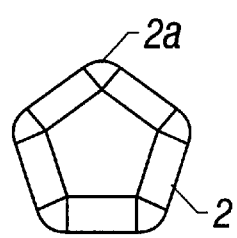

FIGS. 6(e) and 6(f) show the corners of polygon are made arc and quadrangle and pentagon are shown as polygon, which have the same effect.

Figure 6G:
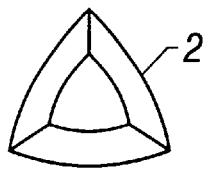
Figure 6H:
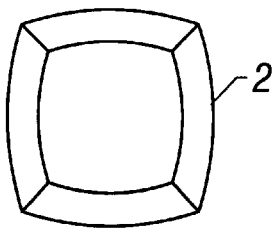

FIGS. 6(g) and 6(h) show each side of the polygon is arc and triangle and quadrangle are shown as polygon, which have the same effect.

Figure 6I:
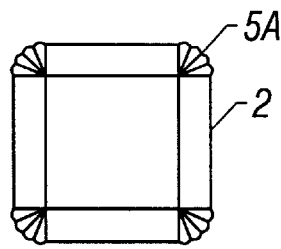
Figure 6J:
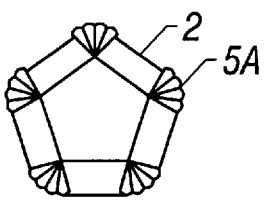

FIGS. 6(i) and 6(j) show the corners of the polygon are formed by the gores in the shape of bellows and quadrangle and pentagon are shown as examples. The shape of bellows means that a number of small gores are formed. The effect of the gores are already explained and when the gores are in the shape of bellows the same effect can be achieved.

Figure 6K:
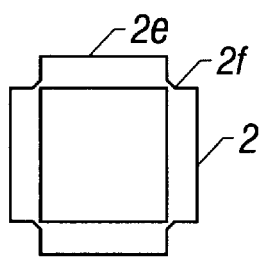
Figure 6L:
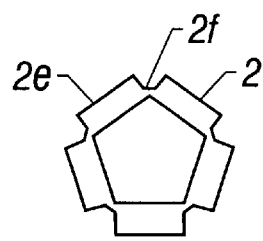

FIGS. 6(k) and 6(l) shows inflation-type frame edges formed by communicating a plural inflation-type cylindrical elements and quadrangle and pentagon are shown as an example. In case of quadrangle, four circular cylindrical bodies 2e are communicated by each other through respective fluid passages 2f that are short and small in diameter. And when a quadrangle is set up, the circular cylinders will stretch uniformly inside and outside, with the frame edge inflated to a specific shape with a lower pressure. Therefore, the necessary amount of fluid required for inflation can be reduced.

The theoretical study of the effect of the polygonal shape hasn't sufficiently done yet. After trial and error of the present inventors, followings will be guessed.

In case of circle, the outer and the inner diameters of the circle become large due to the inflation of the section and both of the outer and the inner circumferences also become long. Extra elastic force is required to extend the sheet material in the direction of circumference as much as the diameter enlarges and the circumference becomes long. Extra pressure is also required to be inflated accordingly. In case of polygon, it is theoretically thought that extra force for extending the length of the cylinder constructing each side of the polygon isn't produced even if the section is inflated. Therefore, the section of polygonal shape can be easily inflated with low pressure comparing to circle.

It can be expected that the inflation-type frame edge shown in FIGS. 6(k) and 6(l), wherein polygon is formed by communicating a plural inflation-type cylindrical elements is advantageous. However, it is hard to produce the inflation-type frame edge shown in FIGS. 6(k) and (l). If highly effective difference is expected corresponding to the productive difficulties, such frame edge can be adopted.

When the frame edge surface is designed to be inflated uniformly, a desirable shape can be obtained with lower pressure and less amount of fluid.

Moreover, the frame edge surface is designed so as not to inflate further after a fixed shape is obtained, the problems of the present invention can be solved effectively because extra pressure and extra fluid aren't required. Therefore, if the frame edge is made of the sheet material with less stretchability which is different from the material of the endo-bag body, a desirable shape is maintained without applying extra pressure and ideal expanded and opened shape can be kept because of the small stretchability. The frame doesn't store extra fluid when inflated, therefore, the fluid leaked in the abdominal cavity out of the bag can be minimized and the influence of pressure on the patient's body can be also minimized even if the bag is broken.

Figure 7A:
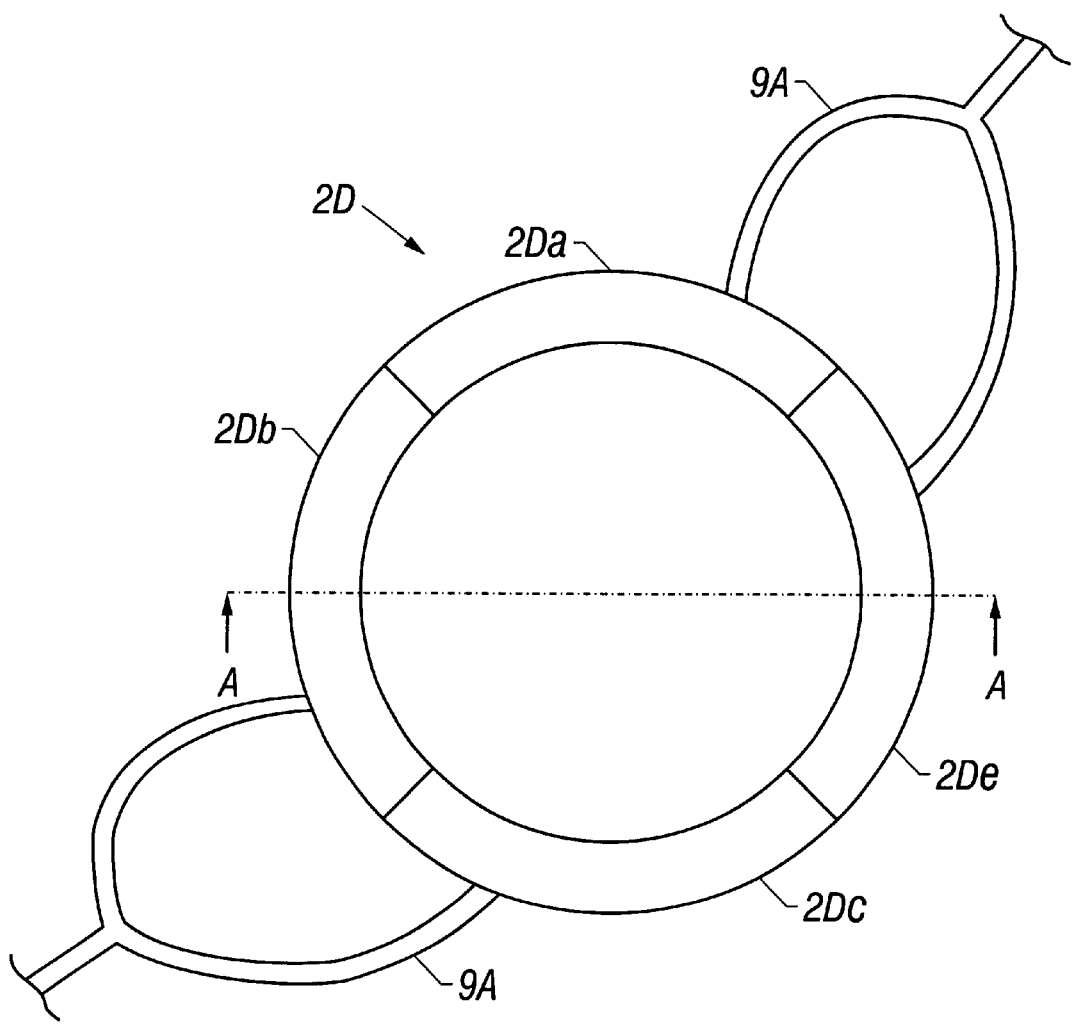
FIG. 7(a) is a front view of the inflation-type frame edge divided into segments and FIG. 7(b) is a sectional view along the line A—A.
Figure 7B:
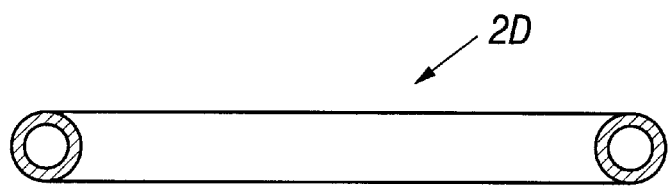

FIG. 7(a) is a front view of the inflation-type frame edge divided into segments and FIG. 7(b) is a sectional view along the line A—A.

The inflation-type frame edge 2D is an improved type of the frame edge as shown in FIGS. 6(k) and 6(l). Four divided segments 2Da–2De, which are provided independently, are connected and each segment is connected with a tube 9A for supplying a fluid respectively. When the frame edge is comprised of a plural divided segments, each segment 2Da–2De can be expanded uniformly with smaller pressure.

The number of the segments isn't limited to four and the formed shape isn't limited to a circle. Various shapes as shown in FIG. 6 can be formed also in this case. Such segments can be communicated each other without provided independently. The tube for supplying a fluid isn't limited if the tube can supply a fluid to all segments and the divided way isn't limited to this embodiment.

Next, examples of the other gores formed by three-dimensional cutting will be explained.

Figure 8A:
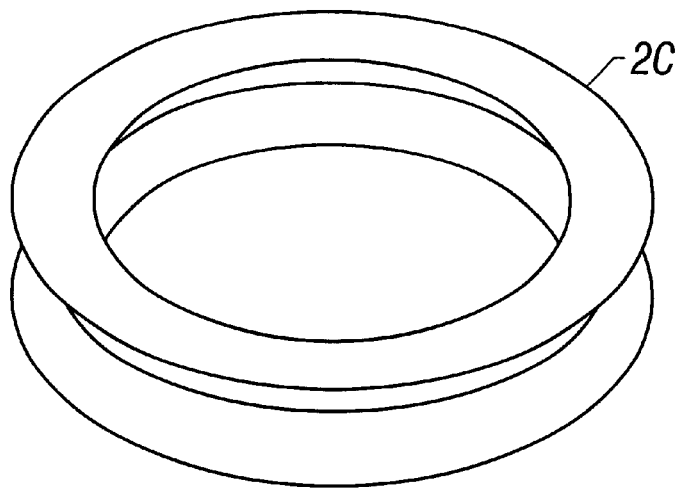
FIG. 8(a) is an external perspective view of a circular inflation-type frame edge provided with gores.
Figure 8B:
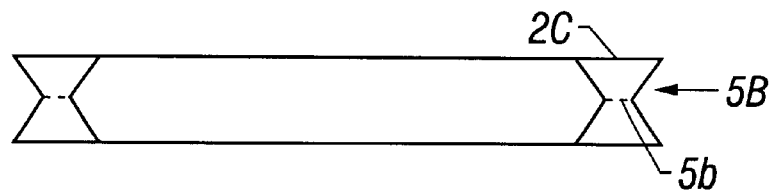
FIG. 8(b) is its sectional view.
Figure 8C:
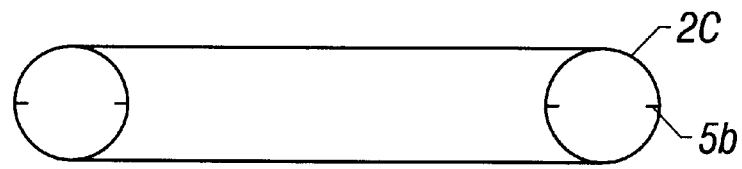
FIG. 8(c) is a sectional view of the inflated frame edge.

FIG. 8 explains the idea of other gore parts of the inflation-type frame edge of the endo-bag of the present invention and FIG. 8(a) is an external perspective view of a circular inflation-type frame edge provided with gores, FIG. 8(b) is its sectional view, and FIG. 8(c) is a sectional view of the inflated frame edge.

In the figures the inflation-type frame edge 2C is taken out for explaining the function of the gore 5B. A fixed space is shown in the inflation-type frame edge 2C so as to easily indicate the gore 5B, however, in fact, the frame edge 2C is flat when a fluid isn't pumped therein.

The inflation-type frame edge 2C is made of pliable sheet such as a urethane sheet which is the same as other inflation-type frame edges explained above. In this case, the sheet material is three-dimensionally cut so as to be a circular doughnut when inflated. The gore 5B, like the ones formed when the lantern is folded, is provided at the inner circumference and the outer circumference between the upper sheet and the lower sheet. The joint 5b of the sheet material produced when the gore 5B is formed is provided inside of the inflation-type frame edge 2C.

When a fluid is pumped in such an inflation-type frame edge 2C, the frame edge 2C is inflated to become like a doughnut as a whole and its section is circular. In this case, the inflation-type frame edge 2C can be inflated with less pressure comparing to the case that the sheet isn't cut three-dimensionally without having the gore 5B and the frame is made circular instead of quadrangular in FIG. 5(a). It is because that the elasticity of the sheet doesn't require extra expanding pressure since the sheet is cut three dimensionally so as not to produce extra flexibility along the three-dimensional shape of the expanded frame.

The joint 5b is designed to be inside when the frame is inflated, so that the abdominal cavity can't be damaged by the joint 5b.

Figure 9A:
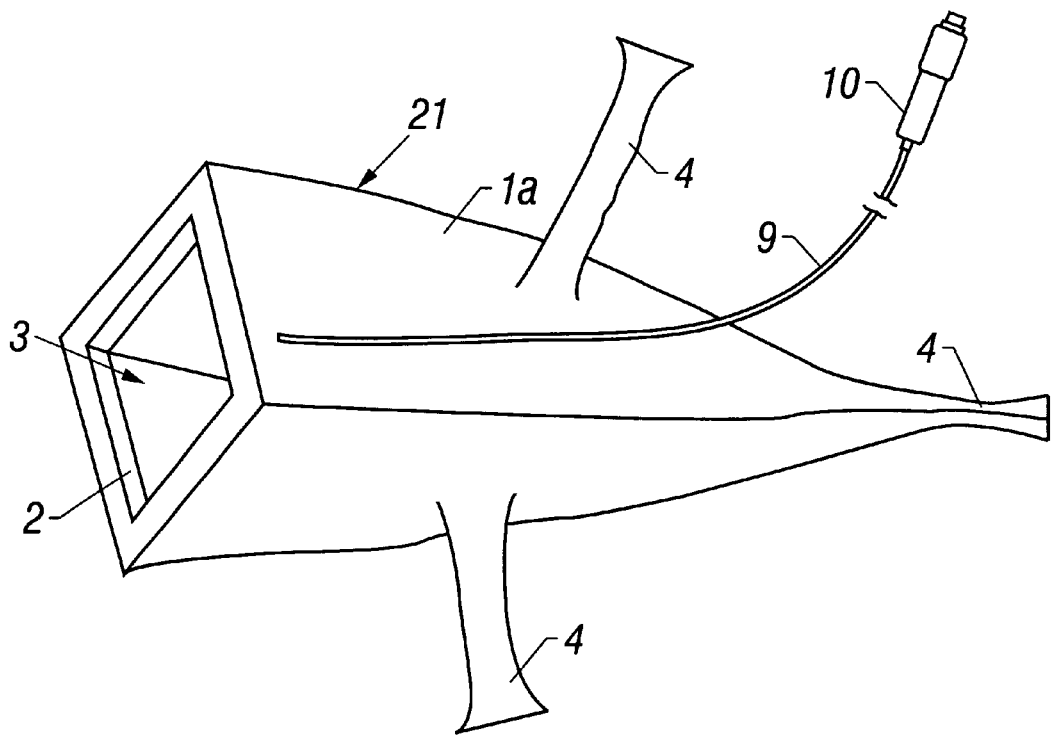
FIGS. 9(a) and 9(b) show external view of the another embodiment of the endo-bag of the present invention.
Figure 9B:
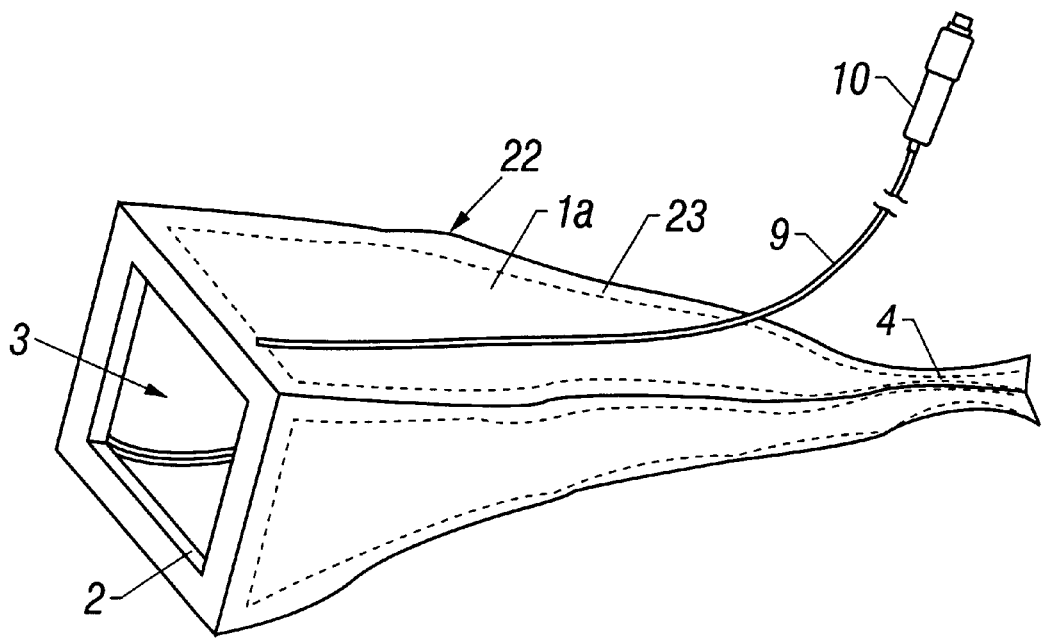
Figure 10A:
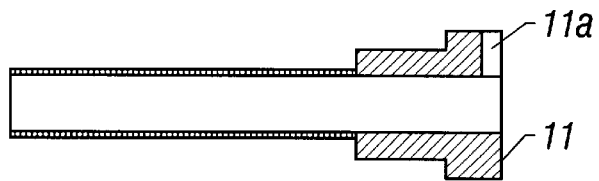
FIG. 10(a) is a vertical sectional view of a guide cylinder.
Figure 10B:
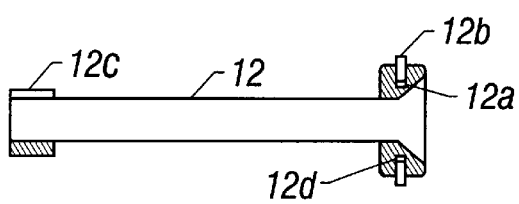
FIG. 10(b) is a vertical sectional view of a push shaft.
Figure 10C:
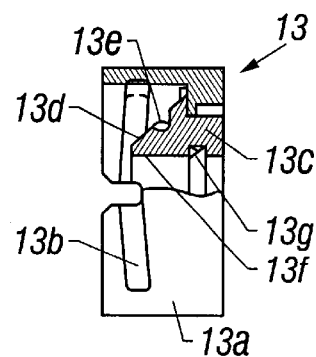
FIG. 10(c) is a partially broken view of a bag fixing cap.
Figure 10D:
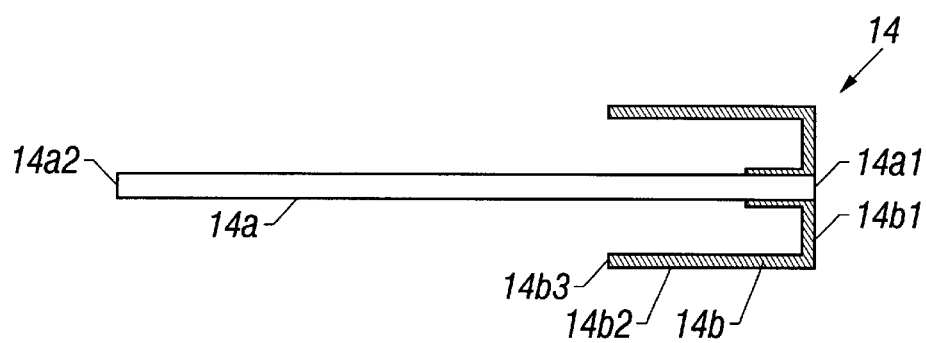
FIG. 10(d) is a vertical sectional view of a forceps guide.

FIGS. 9(a) and 9(b) show external view of the another embodiment of the endo-bag of the present invention.

The endo-bag 21 in FIG. 9(a) is provided with an inserting portion for a surgical instrument 4 on the opposite side of the organ receiving mouth 3 of the receptacle portion 1a and further provided with two inserting portions for a surgical instrument 4 at side walls of the receptacle portion 1a of the endo-bag 21.

According to the inserting portion for a surgical instrument 4 provided on the opposite side of the organ receiving mouth 3, it is convenient that the removed organ B is taken in the bag 21 from the organ receiving mouth 3 by inserting the forceps from the portin 4 as explained for FIG. 1. Further according to other inserting portions for a surgical instrument 4, it is convenient for observation and operation when a laparoscope, an electric surgical knife and an organ cutting device are inserted through a trocar other than the forceps so as to treat the removed organ B taken in the bag 21 such as fine cutting.

The endo-bag 22 in FIG. 9(b) is provided with a plural inflation-type rib frames 23 on the circumferencial wall of the bag 1a running from the organ receiving mouth 3 toward the inserting portion for a surgical instrument 4 and communicating with the inflation-type frame edge 2.

The organ receiving mouth 3 opens at the polygonal inflation-type frame edge 2. At the same time, the whole bag flares out in a form just like a megaphone of which length is small (with sharp inclination). That is, when the organ receiving mouth 3 opens, the bag simultaneously stands ready to take in the organ conveniently without standing the mouth 3 by means of the forceps.

Next the instrument for inserting endo-bag of the present invention into abdominal cavity or thoracic cavity will be explained hereinafter.

FIG. 10 shows one embodiment of the parts comprising the instrument for inserting endo-bag of the present invention. FIG. 10(a) is a vertical sectional view of a guide cylinder, FIG. 10(b) is a vertical sectional view of a push shaft, FIG. 10(c) is a partially broken view of a bag fixing cap, and FIG. 10(d) is a vertical sectional view of a forceps guide.

In FIG. 10, the reference numeral 11 indicates a guide body, 12 is a push shaft, 13 is a bag fixing cap, and 14 is a forceps guide. All of them are made of stainless steel because of its chemical stability, safety for human body, and rust proof characteristics. Other rigid material such as nylon and hard polyvinyl chloride may be used. The instrument for inserting endo-bag is mainly comprised of the guide body 11, and the push shaft 12, the cap for closing the bag 13. The forceps guide 14 is assistantly used.

The guide cylinder 11 is cylindrical and is provided with a stepped brim outside of one side and an escape groove 11a is formed for passing the tube 9 of the endo-bag 1, as shown in FIG. 1, at the end of the brim. The outer diameter of the cylindrical body is set so as to be inserted in the trocar site F (FIG. 1). The endo-bag is folded and contained in the guide cylinder 11 and the tube 9 extending therefrom is led out through the escape groove 11a.

The push shaft 12 is cylindrical so as to be inserted in the guide body 11 and provided with a brim at both sides of the outer circumference thereof. The outer diameter of one brim is set so as to be inserted in the guide body 11 without having any space. The folded and contained endo-bag 1 in the guide body 11 can be pushed out by inserting the push shaft 12 to the guide body 11 with the side having brim heading forward. An escape groove 12c is provided for the outer circumference of the brim for escaping the tube 9 extending from the endo-bag 1.

The outer diameter of the other side of the brim 12d is sufficiently larger than the inner diameter of the guide body 11 and the push shaft 12 is prevented from further inserting by the brim 12d when the push shaft 12 is inserted in the guide body 11. The inner diameter of the brim 12d is formed with a tapered female part 12a which is tapered from the edge of the brim 12d to the inner diameter and the outer circumference thereof is provided with guide pins 12b at two positions.

The cap for fixing the bag 13 is used for covering the brim 12d positioned at the guide pin 12b side of the push shaft 12. The cap 13 is mainly comprised of an outer body 13a and an inner body 13c, both of which are fixed in the axial direction each other and connected rotatably around the axis. Therefore, the outer cap body 13a can be turned without turning the inner cap body 13c.

The outer cap body 13a is cylindrical having a brim in the direction of the inner diameter at one side and the cylindrical body without having the brim is covered on the brim 12d having the guide pin 12b of the push shaft 12. The cylindrical body is provided with two guide grooves 13b which is cut into from the edge and is comprised of a straight groove along the axis and a tapered groove extended from the straight groove. The guide pin 12b is designed to be inserted into the guide groove 13b.

The inner cap body 13c is connected to the inner diameter of the brim of the outer cap body 13a and a tapered male part 13d is formed corresponding to the tapered female part 12a of the push shaft 12. When the push shaft 12 is covered with the cap 13, the tapered female part 12a and the tapered male part 13d are designed to be caught each other. An O-ring 13e is inserted into the groove provided at appropriate parts of the tapered male part 13d.

The inner diameter of the inner cap body 13c is formed as an inserting hole 13f for passing through the shaft of the forceps guide 14 and the forceps without having extra space. A sealing ring 13g is provided at an appropriate portion of the hole 13f to achieve sealing function when the forceps is pierced.

The forceps guide 14 is formed such that a pipe shaft 14a is stood up from the center of the bottom 14b1 of the brim 14b which is U-shaped formed by folding a rectangular plate in longitudinal direction. The guide 14 is used for guiding the endo-bag 1 when it is folded and contained in the guide body 11 and is designed to insert the shaft body of the forceps into its pipe.

The brim 14b of the forceps guide 14 is comprised of the bottom 14b1 from which the pipe shaft 14a is stood up and sides 14b2 extending parallel to the pipe shaft 14a from the both edges of the bottom 14b1. The reference numeral 14b3 indicates the end of the side 14b2, 14a1 indicates the end of the pipe shaft 14a at the bottom 14b1 side, and 14a2 indicates the other end.

FIG. 11 explains the seal mechanism of the instrument for inserting endo-bag. FIG. 11(a) shows when the inserting portion of the surgical instrument of the endo-bag is passed through the push shaft, FIG. 11(b) shows the state before the end of the inserting portion is fixed with the cap, FIG. 11(c) shows its section, FIG. 11(d) shows the state after the inserting portion is fixed, and FIG. 11(e) shows its section.

The end of the inserting portion for surgical instrument 4 of the endo-bag 1 is passed through the inside of the push shaft 12 and is turned down so as to cover the outer circumference of the brim of the push shaft 12 and the cap 13 is covered on the turned-up portion (FIG.11(a)).

Then the guide groove 13b of the cap 13 is inserted into the guide pin 12b of the push shaft 12 (FIG. 11(b), (C)).

When the outer cap body 13a is turned clockwise, the whole cap body 13 moves in the direction of the arrow 13A in the figure, namely toward the push shaft 12, because of the connection of the guide groove 13b and the guide pin 12b and the tapered function of the guide groove 13b (FIG. 11(d)).

In this case, the inner cap body 13c rotatably connected with the outer cap body 13a doesn't turn and only moves in the direction of the arrow 13A. According to this movement, the tapered male part 13d of the inner cap body 13c approaches to an appropriate tapered female part 12a of the push shaft 12. The end of the inserting portion for a surgical instrument 4 fasten therewith is fixed to the push shaft 12 because of the O-ring 13e provided for the tapered male part 13d and the sealing between the inserting portion for a surgical instrument 4 and the cap 13 can be kept (FIG. 11(e)).

Under such a condition, when the pipe shaft 14a of the forceps guide 14 or the shaft body of the forceps is inserted into the inserting hole 13f of the cap 13, sealing between the cap 13 and the forceps guide 14 or the shaft body of the forceps can be maintained because of the function of the seal ring 13g provided for the inserting hole 13f. When the shaft body of the forceps is inserted into the forceps guide 14, the forceps guide 14 and the axial body of the forceps can be also sealed.

Accordingly, as a whole, the inserting portion for a surgical instrument 4 is fixed and the inside of the endo-bag 1 is kept airtightly. Further, the fluid such as carbonic acid gas to inflate the bag 1 is prevented from leaking out and influence of the outside air in the abdominal cavity can be minimized because of its excellent sealing ability.

Next, other embodiments of the endo-bag and the surgical instrument for inserting the bag according to the present invention will be explained.

FIG. 12 shows another embodiment of the endo-bag of the present invention. FIG. 12(a) is an external view showing a partial section and FIG. 12(b) is a front view of the sealing plug. In this figure, the same numerals are used for the same parts of the endo-bag as explained above and their explanations are omitted here.

An inserting portion for a surgical instrument 4A of the endo-bag 1B is shorter than the one explained above. It is different from the one explained above in that it is provided with an instrument holder 15 and a sealing plug 16 to be inserted into an inserting hole 15a. The instrument holder 15 and the sealing plug 16 are made of a highly reliable soft rubber such as silicon rubber and their sealing ability is high.

The diameter of the inserting hole 15a is set to fit the outer diameter of the surgical instrument such as a forceps A and extra outside air is prevented from entering when the surgical instrument is inserted or operated. After necessary treatment is finished, the surgical instrument is pulled out and the sealing plug 16 is inserted into the hole 15a. Therefore, leakage out of the endo-bag 1 and entering of a contaminant from the outside air can be prevented by inserting the sealing plug 16 into the hole 15a.

Figure 13A:
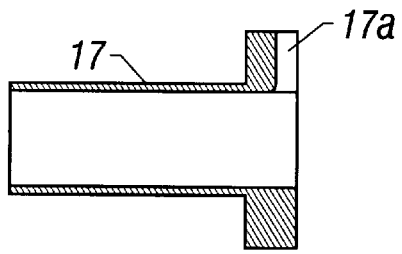
In FIG. 13(a), a guide cylinder, in FIG. 13(b) a push shaft, and in FIG. 13(c) the surgical instrument for inserting the endo-bag are ready to be inserted respectively.
Figure 13B:
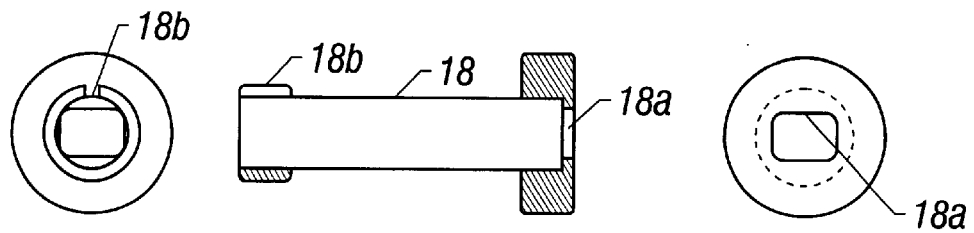
FIG.13 shows another embodiment of the surgical instrument for inserting the endo-bag according to the present invention.
Figure 13C:
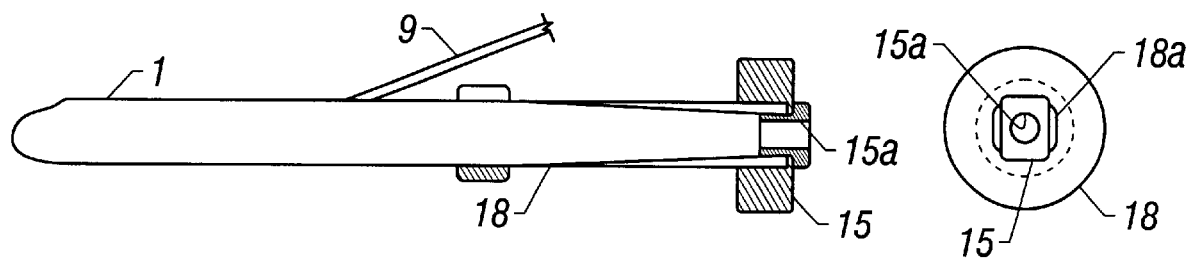

FIG. 13 shows another embodiment of the inserting means for an endo-bag 1B according to the present invention. FIG. 13(a) shows a guide cylinder, FIG. 13(b) shows a push shaft, and FIG. 13(c) shows the condition wherein the inserting means for an endo-bag can be inserted. FIG. 13(b) shows its left side view at left and its right side view at right other than the vertical sectional view at center. In FIG. 13(c) shows its right side view at right other than the sectional view showing its usage at left.

A guide cylinder 17 has the same construction as the guide cylinder 11 in FIG. 10, has an escape groove 17a for the tube 9 and stores the folded endo-bag 1B.

A push shaft 18 has the same construction as the push shaft 12 in FIG. 10 and has an escape groove 18b. They are different in that the inside of the brim isn't formed as tapered and a rectangular fitting hole 18a is provided.

The fitting hole 18a is designed so as to fit the outer shape of the instrument holder 15 provided at the inserting portion for a surgical instrument 4A of the endo-bag 1B, namely the rectangular shape in this case. The instrument holder 15 can be passed through by adjusting the shape thereof. Therefore, when the inserting portion for a surgical instrument 4A of the endo-bag 1B is passed through the inside of the push shaft 18, the shapes of the instrument holder 15 and the fitting hole 18a are matched and the instrument holder 15 is taken out from the fitting hole 18a. After that, those shapes are arranged so as not to be matched as shown in FIG. 13(c) so that the instrument holder 15 is prevented from inserting into the fitting hole 18a and operation by inserting the surgical instrument into the inserting hole 15a can be done concentrately.

When the operation is finished, outer air is prevented from entering and leakage from the endo-bag 1 is also prevented if the above-mentioned sealing plug 16 is inserted into the inserting hole 15a. When the outer shape of the instrument holder 15 and the shape of the fitting hole 18a are matched, the instrument holder 15 can be inserted in the push shaft 18 and the endo-bag 1B can be inserted in the abdominal cavity.

Now, one embodiment of the usage of the endo-bag and the inserting means for the bag according to the present invention will be described.

FIGS. 14–25 show the procedure how the removed organ is taken out by means of the endo-bag of the present invention. FIG. 14(a) shows when the inserting portion for the surgical instrument of the endo-bag is passed through the push shaft, FIG. 14(b) shows when the end of the inserting portion is fixed with the cap, FIG. 15(c) shows when the forceps guide is inserted.

FIG. 16(d) shows the state when the endo-bag is folded, FIG. 16(e) shows when the tip end of the folded endo-bag is bent.

FIG. 17(f) shows when the folded endo-bag is contained in the guide cylinder, and FIG. 17(g) shows setting condition of the endo-bag before it is used.

Figure 18H:
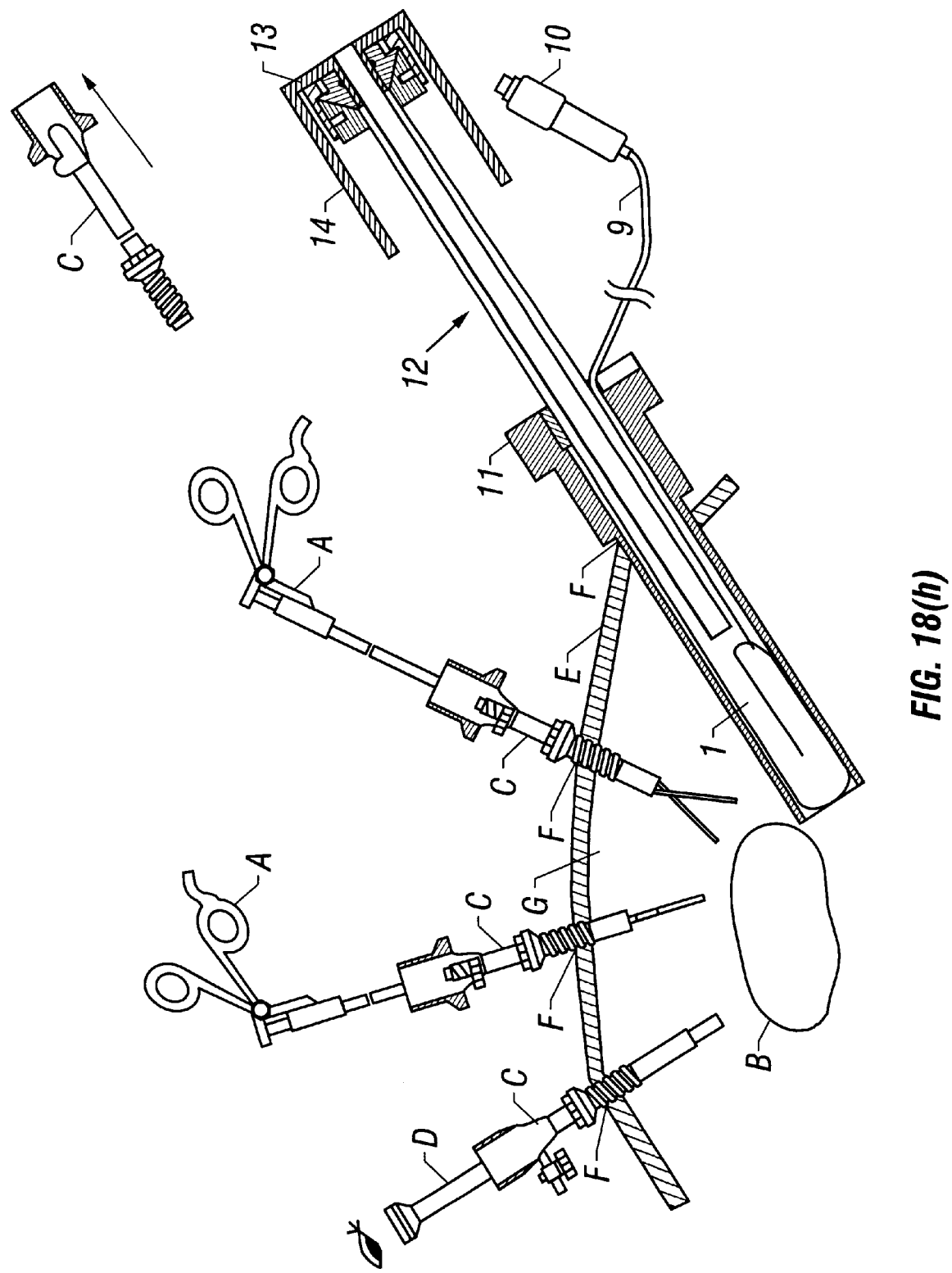
FIG. 18(h) shows how the guide cylinder containing the endo-bag is inserted in the abdomen of a patient in case of endoscopic operation.

FIG. 18(h) shows how the guide cylinder containing the endo-bag is inserted in the abdomen of a patient in case of endoscopic operation.

Figure 19I:
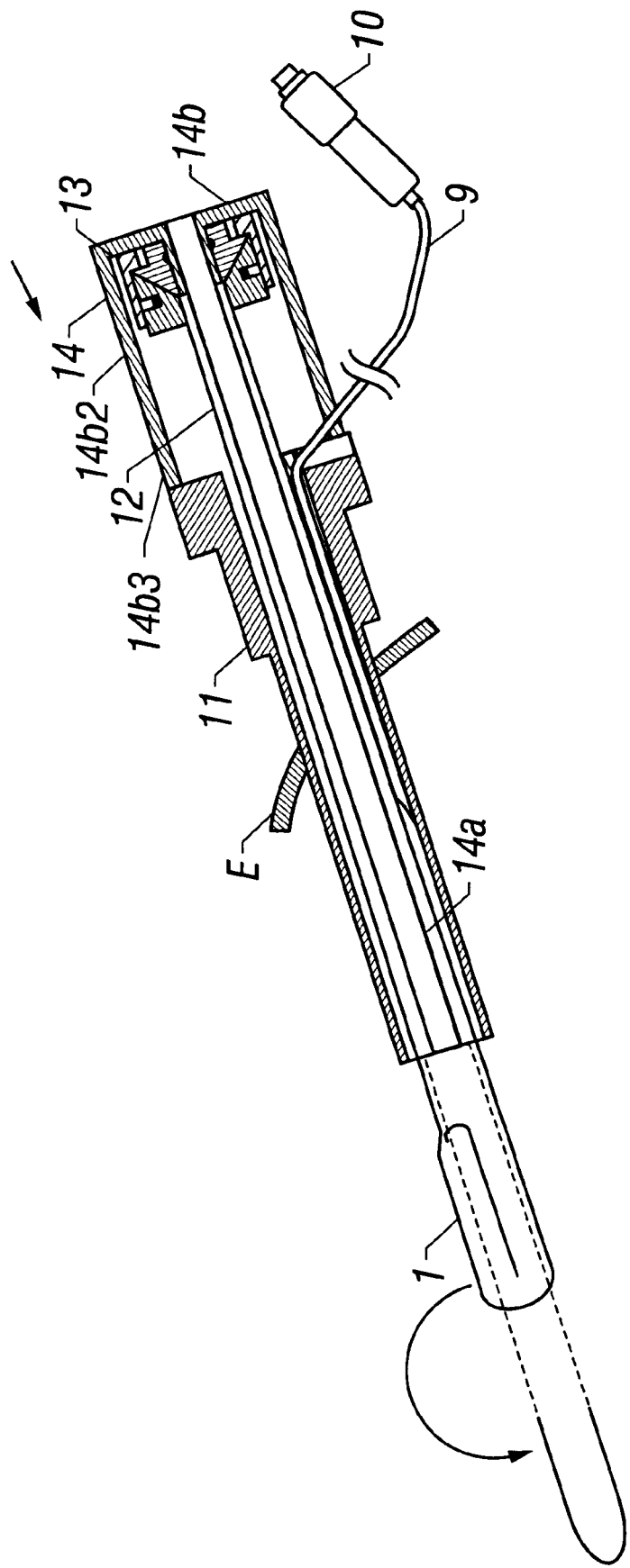
FIG. 19(i) shows how the endo-bag is inserted in the abdominal cavity by means of the push shaft.

FIG. 19(i) shows how the endo-bag is inserted in the abdominal cavity by means of the push shaft.

Figure 20J:
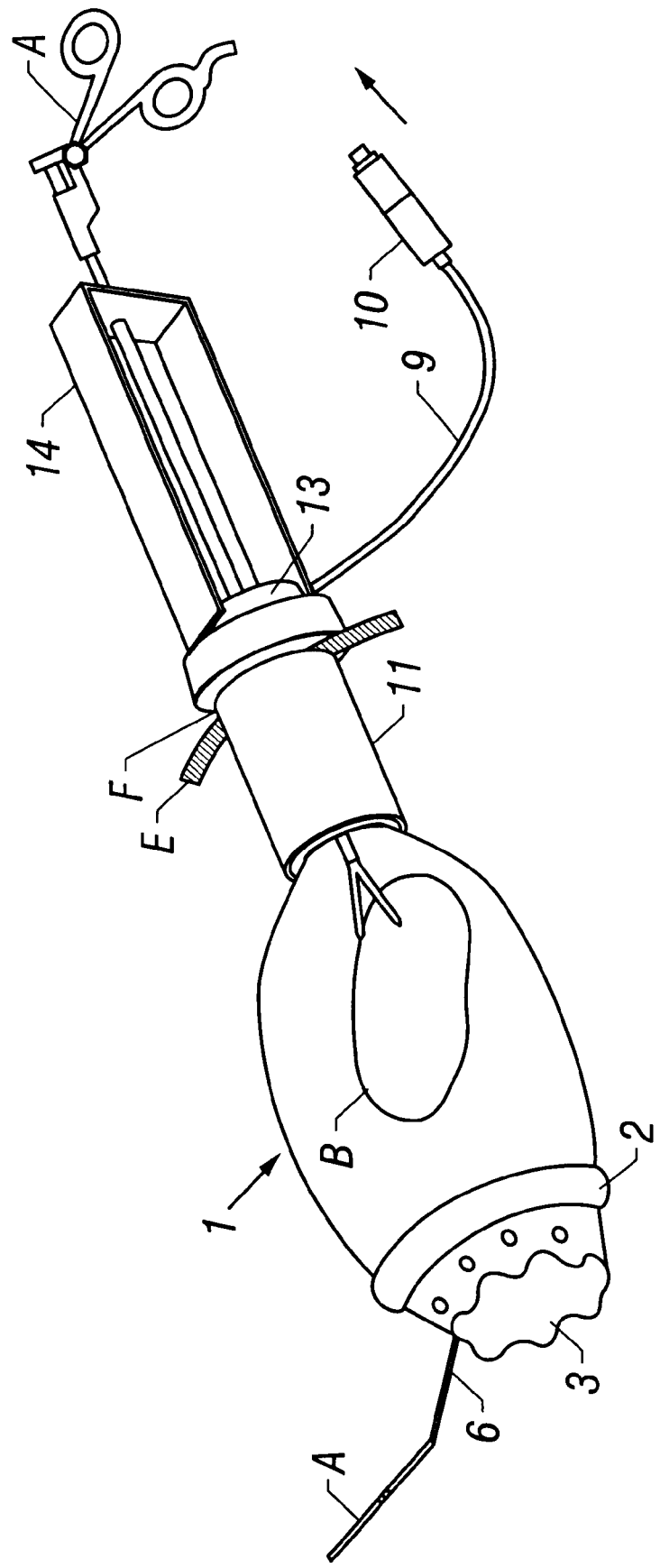
FIG. 20(j) shows when the organ receiving mouth is closed by pulling a closing string after the organ is taken in the endo-bag.

FIG. 20(j) shows when the organ receiving mouth is closed by pulling a closing string after the organ is taken in the endo-bag.

Figure 21K:
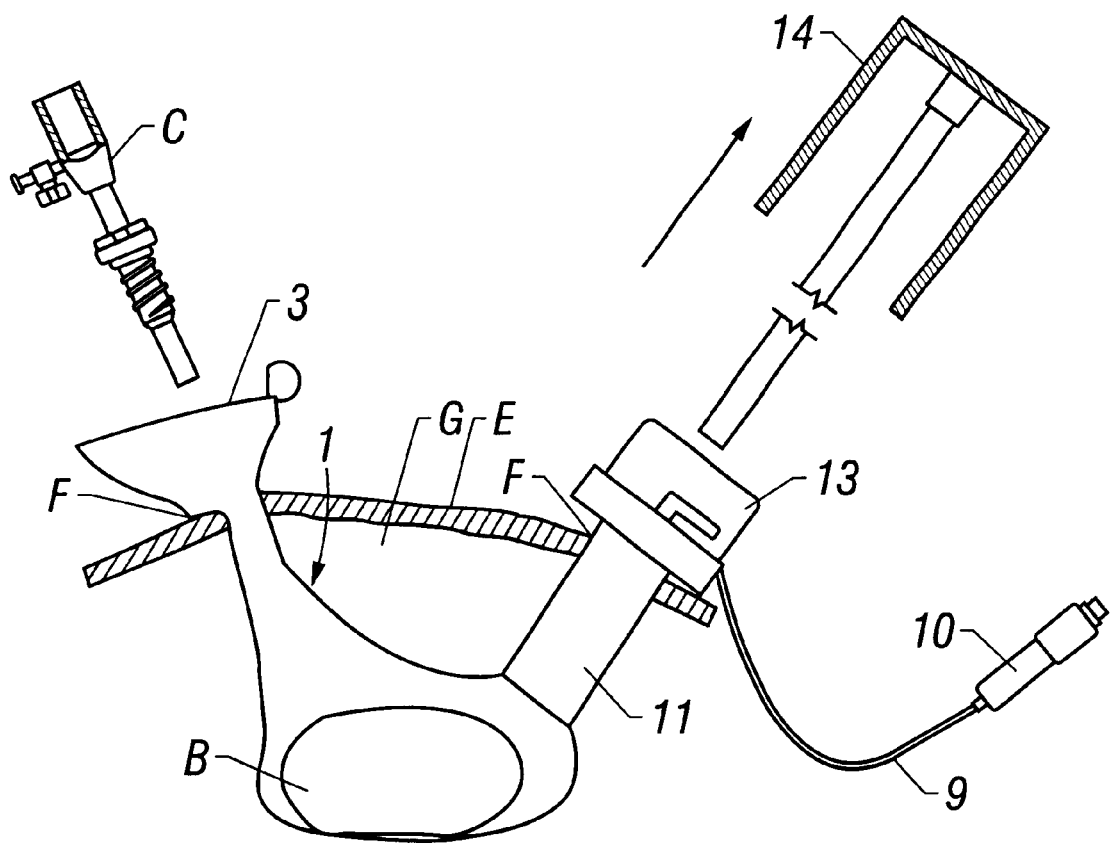
FIG. 21(k) shows how the organ receiving mouth is taken out of the patient's body at the same time a trocar is pulled out of a trocar puncture.

FIG. 21(k) shows how the organ receiving mouth is taken out of the patient's body at the same time a trocar is pulled out of a trocar site.

Figure 22I:
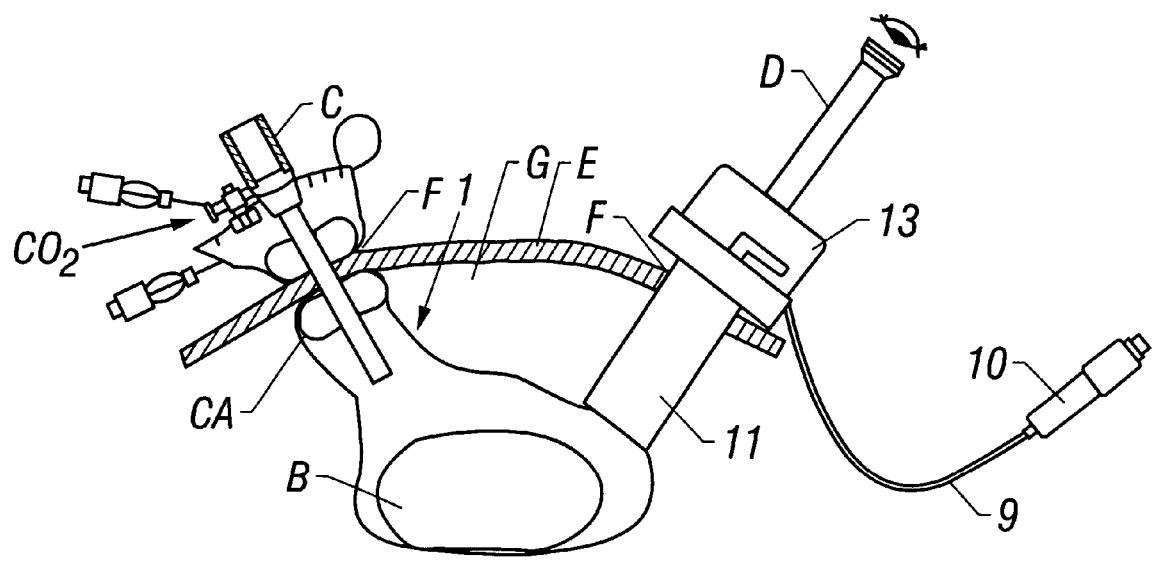
FIG. 22(l) shows when the endo-bag is inflated by pumping carbonic acid gas after a trocar cuff is set.

FIG. 22(l) shows when the endo-bag is inflated by pumping carbonic acid gas after a trocar cuff is set.

Figure 23M:
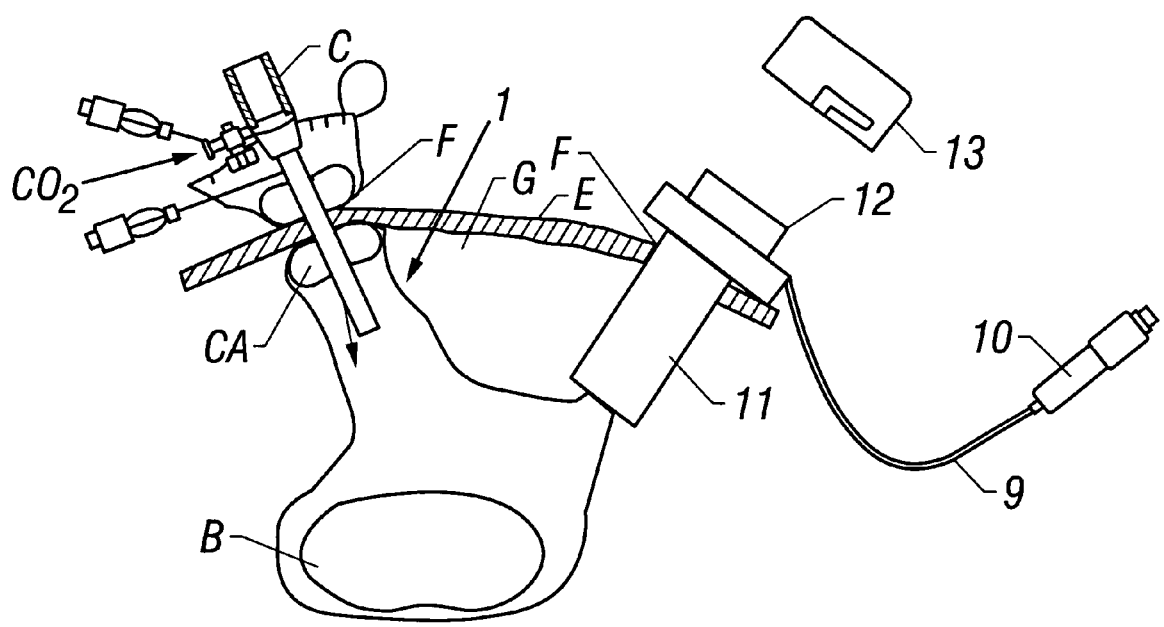
FIG. 23(m) shows when the cap is removed after operation.

FIG. 23(m) shows when the cap is removed after operation.

Figure 24N:
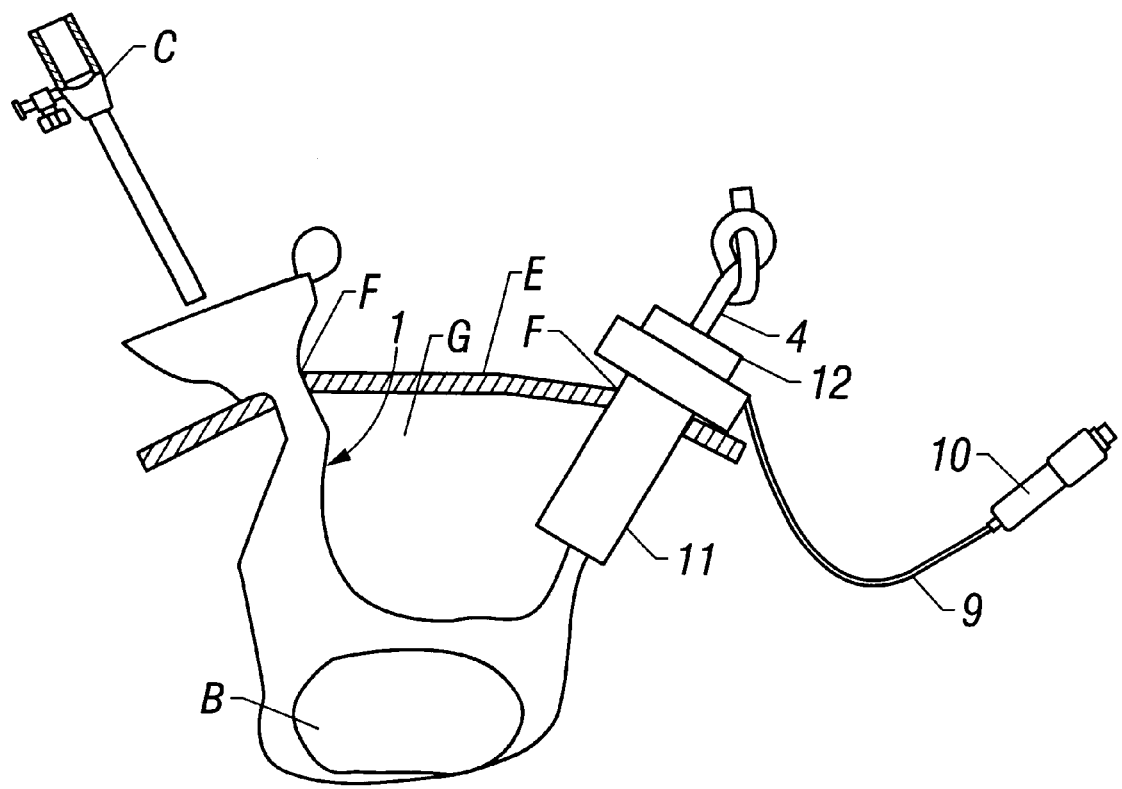
FIG. 24(n) shows when the inserting portion for the surgical instrument is tied so as to prevent the body fluid or the like contained in the endo-bag from leaking out.

FIG. 24(n) shows when the inserting portion for a surgical instrument is tied so as to prevent the body fluid or the like contained in the endo-bag from leaking out.

Figure 25O:
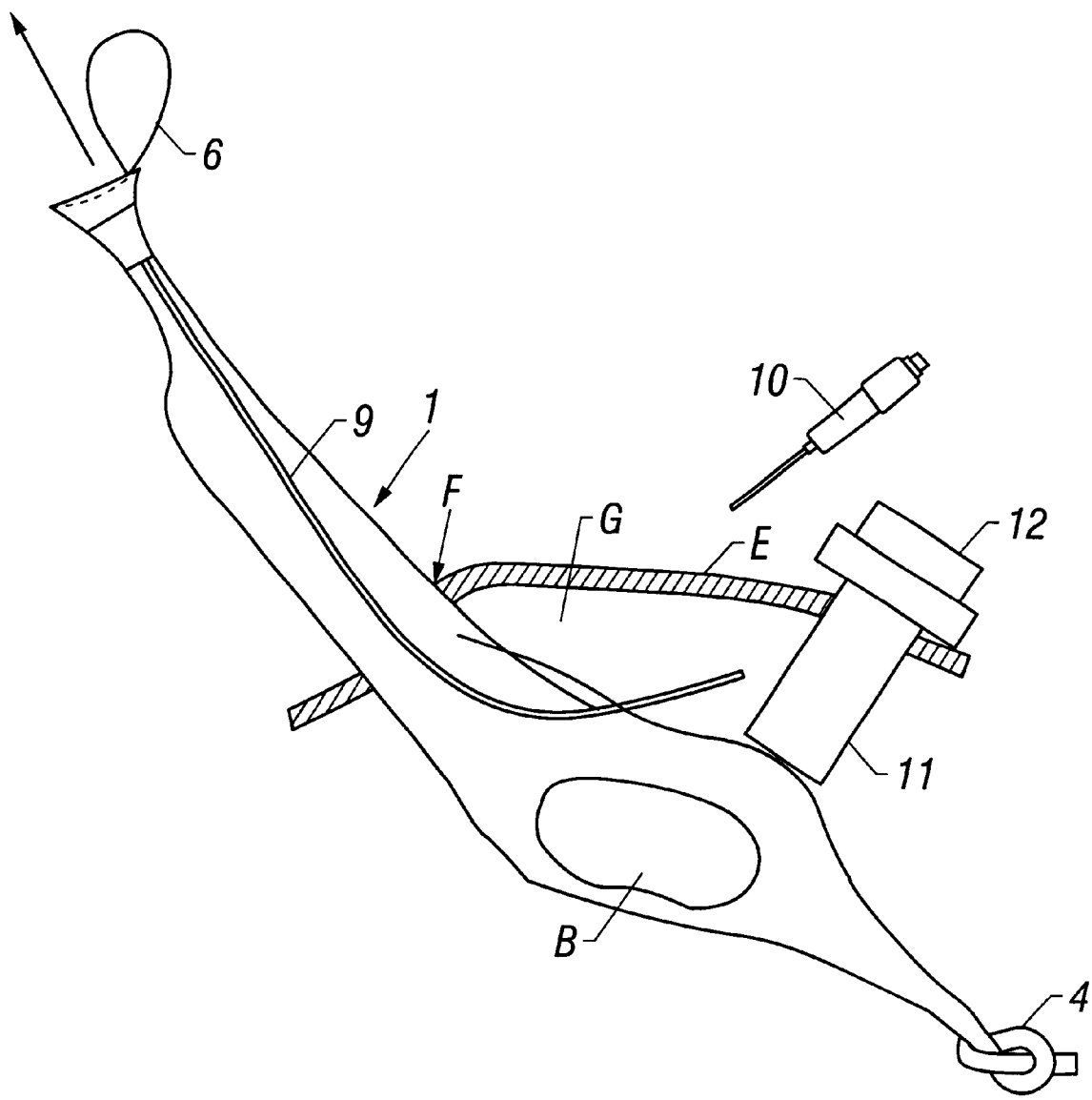
FIG. 25(o) shows when the endo-bag is taken out while containing the removed organ.

FIG. 25(o) shows when the endo-bag is taken out while containing the removed organ.

Figure 14A:
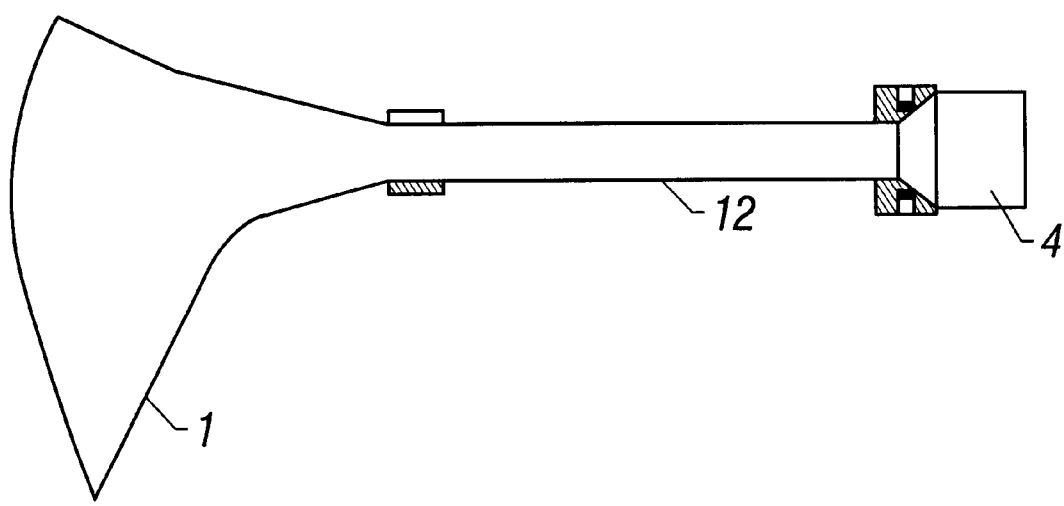
FIG. 14(a) shows when the inserting portion of the surgical instrument for inserting the endo-bag is passed through the push shaft.
Figure 14B:
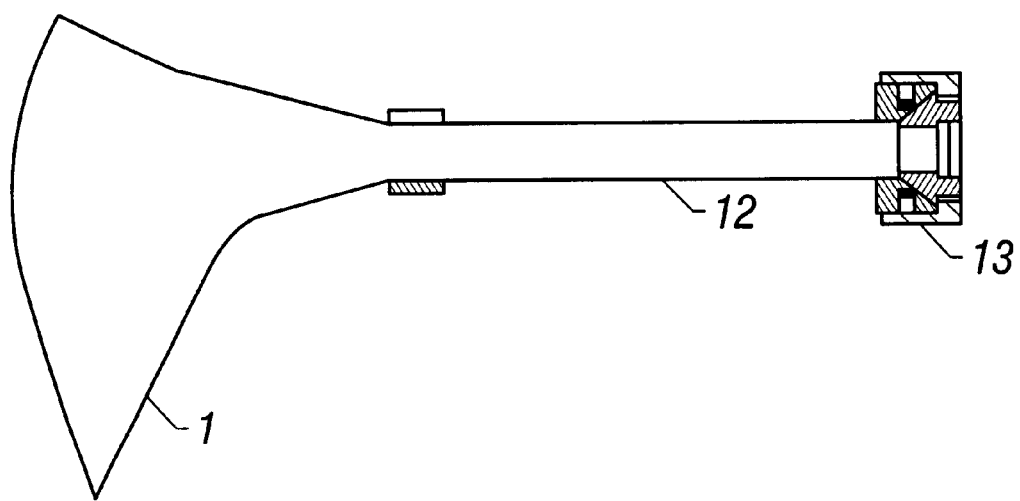
FIG. 14(b) shows when the end of the inserted portion is fixed with the cap.
Figure 15C:
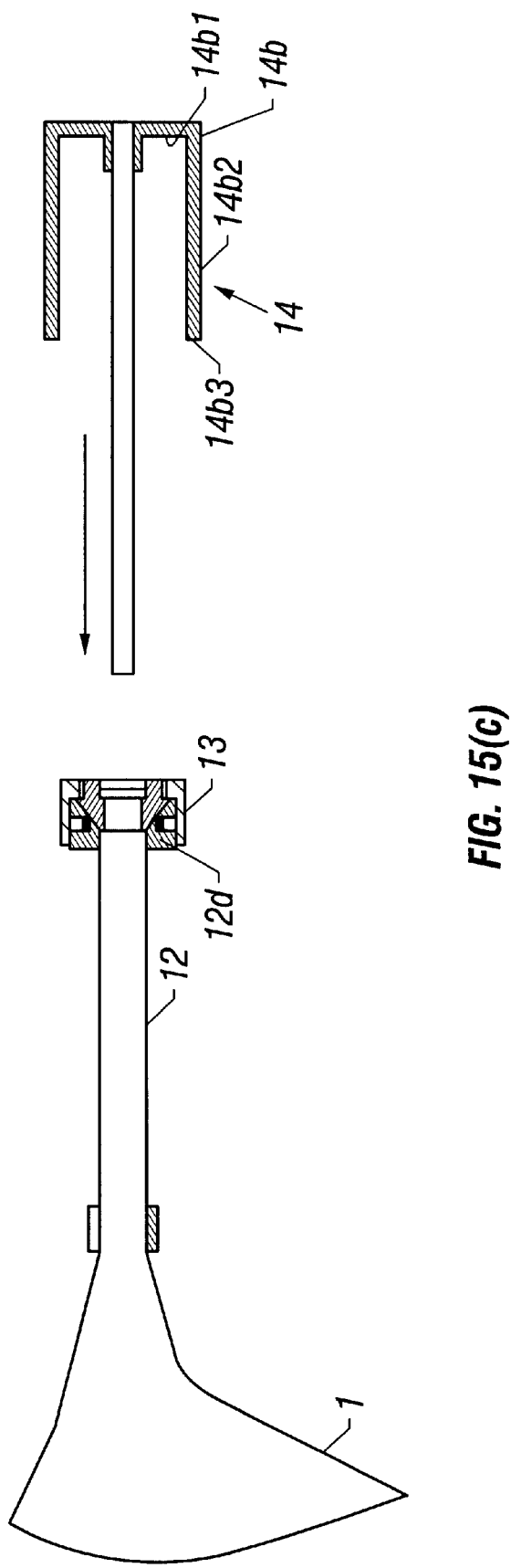
FIG. 15(c) shows when the forceps guide is inserted.

The inserting portion for a surgical instrument 4 of the endo-bag 1 is passed through the push shaft 12 (FIG. 14(a)). Then the end of the inserting portion 4 is held down so as to cover the push shaft 12 and fixed with the cap 13 (FIG. 14(b)). As explained about FIG. 11, fixing of the inserting portion 4 into the push shaft 12 and sealing of the inside of the endo-bag 1 can be easily achieved at the same time by covering the end of the inserting portion 4 with the cap 13 and by turning the cap 13. After that, the forceps guide 14 is inserted into the push shaft 12 in such a manner that the bottom 14b1 of the brim 14 of the forceps guide 14 comes into contact with the cap 13 (FIG. 15(c)).

The length of the side 14b2 of the brim 14b is longer than the longitudinal width of the brim 12d of the push shaft 12 and that of the inserted cap 13. The forceps guide 14 is pushed until the end 14b3 of the side 14b2 of the brim 14b comes in contact with the brim of the guide cylinder 11. After the forceps guide 14 is stopped and the opening of the endo-bag 1 is expanded and opened, only the push shaft 12 is pushed into the organ. In order to secure the distance for containing the organ, the above-mentioned length is set.

Then, the endo-bag 1 is folded in a compact shape (FIG. 16(d)) with the push shaft 12 inserted in the forceps guide 14 and the tip of the folded endo-bag 1 is bent (FIG. 16(e)). The forceps guide 14, the push shaft 12 and the endo-bag 1 are integrally contained in the guide cylinder 11 to the position where the bent portion and the escape groove 12c of the tip of the push shaft 12 are inserted (FIG. 17(f)). In such a manner, the endo-bag 1 is set in the guide cylinder 11 as shown in FIG. 17(g).

The guide cylinder 11 containing the endo-bag 1 is inserted into the trocar site F of a patient's body E instead of the trocar C (FIG. 18(h)). The reference character D indicates a laparoscope. Then, the forceps guide 14 is pushed into the organ and at the same time the push shaft 12 is pushed. As a result, the endo-bag 1 is pushed toward the organ in the abdominal cavity G (FIG. 19(i)).

As the forceps guide 14 is pushed forward, the folded endo-bag 1 is restored into its unfolded shape because of the elasticity itself. The forceps guide 14 stops when the end 14b3 of the side 14b2 of the brim 14b comes in contact with the brim of the guide cylinder 11. In this time, the length of the pipe shaft 14a of the forceps guide 14 is designed so as not to project out of the guide cylinder 11 in order to obtain safety in the abdominal cavity.

Then, a fluid is pumped into the inflation-type frame edge 2 of the endo-bag 1 and the organ receiving mouth 3 is expanded. Only the push shaft 12 is pushed toward the removed organ B, and the removed organ is taken in. These procedures are already described using FIG. 1.

After the removed organ B is completely taken and contained in the bag 1, a fluid is taken out of the inflation-type frame edge 2 to be shrunk and the organ receiving mouth 3 is closed by pulling the closing string 6 (FIG. 20(j)).

Then the trocar C is pulled out of the trocar site F and simultaneously the organ receiving mouth 3 is taken out of the body (FIG. 21(k)).

The trocar cuff CA is set between the endo-bag 1 and the trocar C and sterilized distilled water is pumped from each of two water inserting ports of the trocar cuff CA so as to inflate the trocar cuff CA and to keep the airtight sealing between the trocar C, the endo-bag 1, and the trocar site F. Then carbonic acid gas (CO2) is pumped from a gas inserting port of the trocar C so that the inside of the endo-bag 1 in the abdominal cavity G is inflated (FIG. 22 (l)). As a result, a fixed space is produced in the endo-bag 1 and visual field in the laparoscope can be obtained to facilitate operation.

After necessary treatment is done, the cap 13 is removed so that the inserting portion for a surgical instrument 4 of the endo-bag 1 can be inserted in the abdominal cavity G (FIG. 23 (m)).

The inserting portion for a surgical instrument 4 is tied and closed so as to prevent the body fluid from leaking out of the endo-bag 1 (FIG. 24(n)).

Finally, the tube 9 is cut, the inserting portion for a surgical instrument 4 is inserted in the abdominal cavity G, and the endo-bag 1 containing the removed organ B is taken out of the trocar site F (FIG. 25(o)).

According to the endo-bag and the inserting means for an endo-bag of the present invention, the endo-bag can be inserted in the abdominal cavity easily and safely. Further, the organ receiving mouth can be expanded and opened at low pressure and with small amount of fluid easily and safely and is hardly deformed. Therefore, removed organ can be taken in the bag quickly and they are suitable for endscopic operation.

Now, still another embodiment of the endo-bag and the inserting means for an endo-bag of the present invention will be explained hereinafter with reference to the accompanying drawings.

Figure 26:
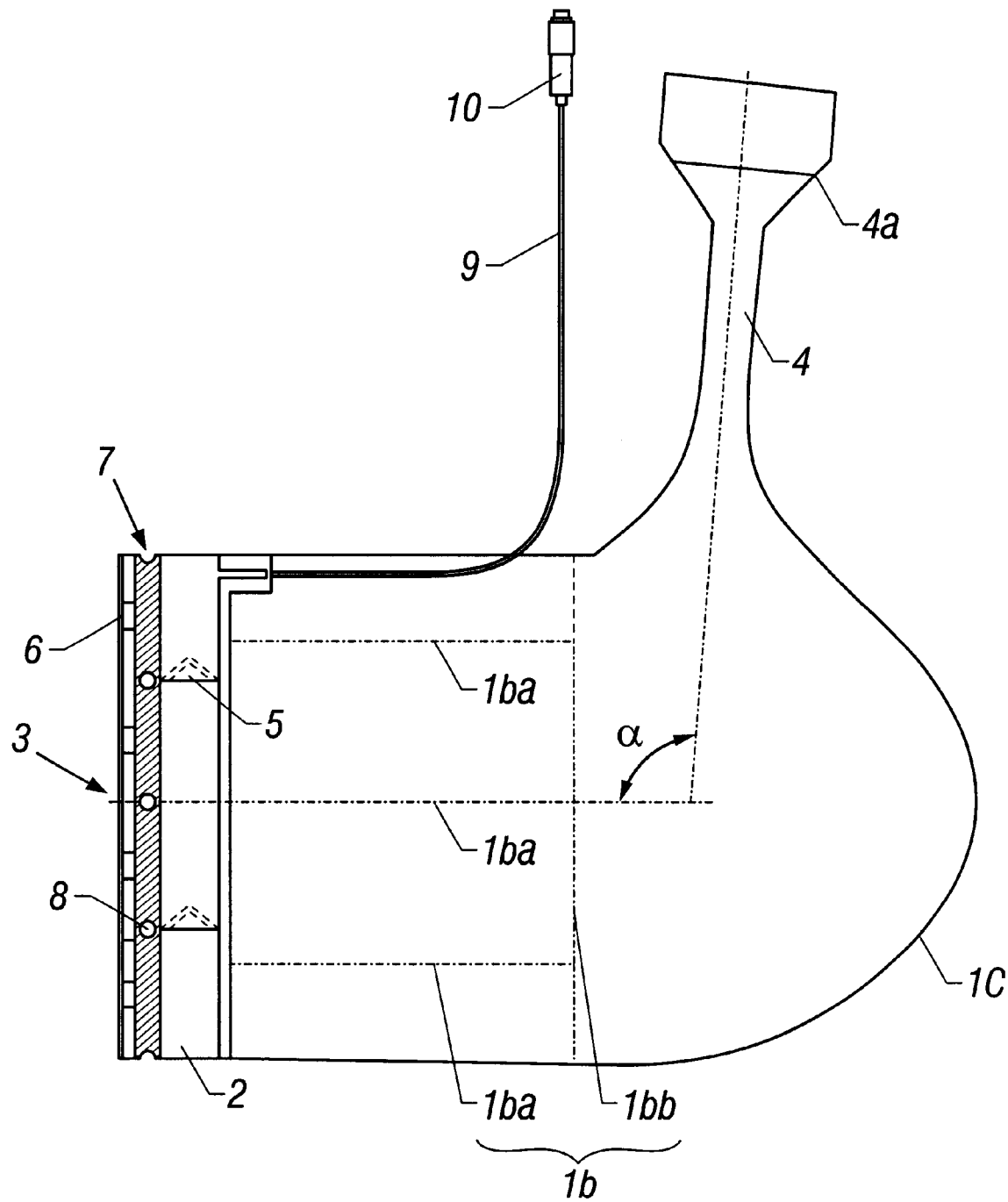
FIG. 26 is an external plan view of another embodiment the endo-bag of the present invention.

FIG. 26 is an external plan view of another embodiment of the endo-bag of the present invention. The same numerals are used for the same parts as explained above and their explanation is omitted hereinafter.

The endo-bag 1C is different from the endo-bag 1 of FIG. 2 in that the receptacle portion 1a has folding lines 1b to be folded. Further, the angle α defined by the inserting portion for a surgical instrument 4 and the longitudinal center line of the receptacle portion 1a is different.

The folding lines 1b are shown as two-dotted lines in the figure, however, they are actually formed on the sheet material of the receptacle portion 1a as an aim to show a line to be fold. There are folding lines 1ba which are parallel to the longitudinal direction of the receptacle portion 1a and line 1bb which is vertical to the lines 1ba.

The folding lines 1ba are formed so as to divide the outer circumference of the receptacle portion 1a into six portions, the outer circumference of which is perpendicular to the longitudinal direction of the receptacle portion 1a. In the figure, only one side is seen. The folding lines 1ba are only an aim to fold the endo-bag 1C when it is inserted in the guide cylinder, as mentioned hereinafter. The outer circumference is divided into six in this case, however, the number is appropriately set according to how the bag is folded.

The folding line 1bb is an aim to fold the back of the line 1bb of the receptacle portion 1a into the organ receiving mouth 3 side and is formed around the outer circumference in the direction perpendicular to the longitudinal direction of the receptacle portion 1a.

The angle α defined by the inserting portion for a surgical instrument 4 and the longitudinal center line of the receptacle portion 1a isn't shown in the endo-bag 1 in FIG. 2, however, it is 150°~160°. The angle α of the endo-bag 1C is 90°~100°. The reason of setting such an angle is as follows. As shown in FIG. 21(k) and FIG. 22(l), when the endo-bag 1C is set in the abdominal cavity, the positional relation between the inserting portion 4 and the organ receiving mouth 3 conforms to the relation between the trocar sites to be formed respectively so that the endo-bag 1C has no slag and wrinkles on operation.

In such a manner, the slag can't hinder the visual range of the endscope D when several treatment is done in the endo-bag 1C. Further, the surgical instruments can't be caught by the slag and the endo-bag is prevented from being broken. Moreover, enough treatment space in the endo-bag 1C is obtained and treatment therein can be facilitated.

The thick line 4a formed at the edge of the inserting portion for a surgical instrument 4 is, as explained hereinafter, an aim for turning down when the inserting portion 4 is inserted in the push shaft and sealed with the cap. The line is colored by an appropriate coloring means as a mark.

Figure 27A:
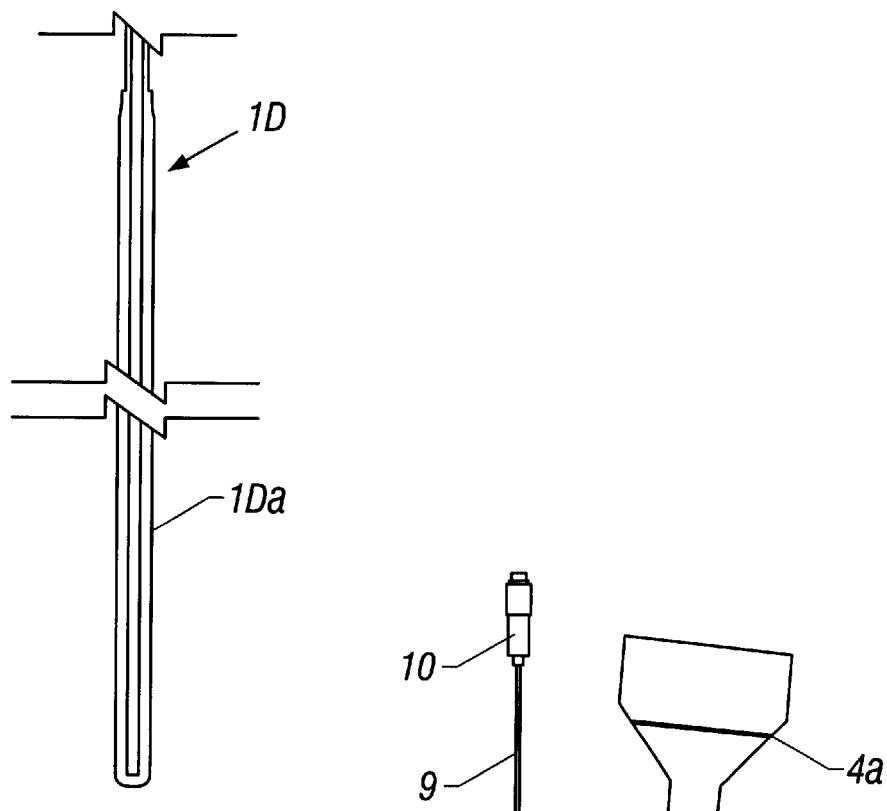
FIG. 27(a) is a sectional view along the line A1 of the still another embodiment of the endo-bag of the present invention and FIG. 27(b) is its external plan view.
Figure 27B:
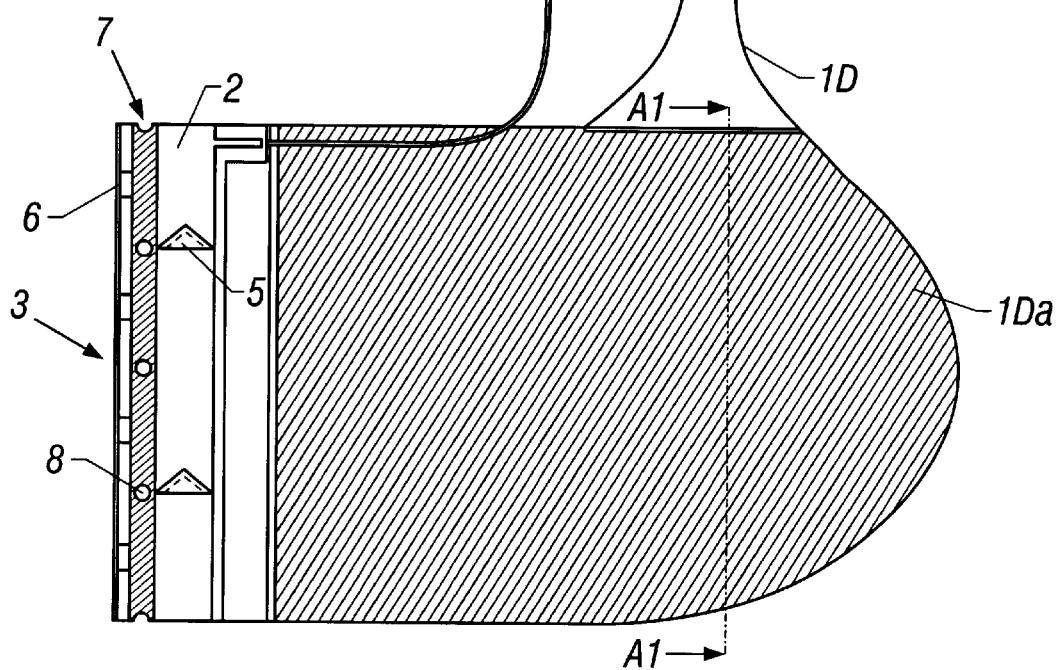

FIG. 27(a) is a sectional view along the line Al of the still another embodiment of the endo-bag of the present invention and FIG. 27(b) is its external plan view.

The endo-bag 1D has a double constructed receptacle portion 1Da, as shown in the sectional view of FIG. 27(a) and a plan view of FIG. 27(b) comparing to the endo-bag IC of FIG. 26.

The receptacle portion 1Da is double constructed so as not to give adverse effect of the contained organ on the abdominal cavity even if one of the inner and the outer bags is broken under endoscopic operation. Accordingly safety of endoscopic operation can be more improved.

Then, a guide cylinder 11A, a grip plug 11B, a push shaft 12A provided with a pipe guide 12B, a cap for folding 12C, a bag fixing cap 13A, and a forceps guide 14A, all of which are used for inserting the endo-bag iC of FIG. 26 and the endo-bag 1D of FIG. 27 into the abdominal cavity. They corresponds to the guide cylinder 11, the push shaft 12, the bag fixing cap 13, and the forceps guide 14 respectively and only the difference will be detailed.

Figure 28A:
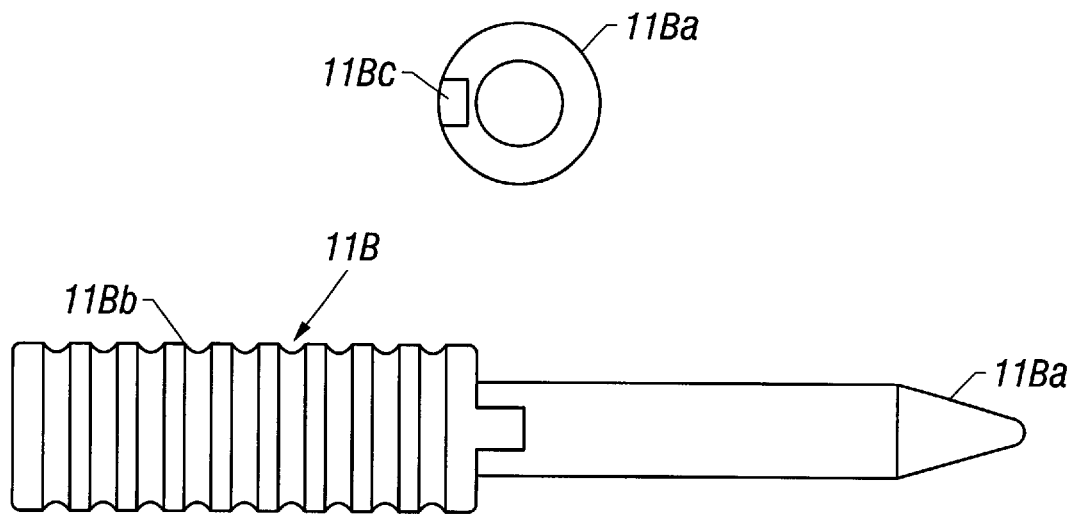
FIG. 28(a) is a front view of the grip plug.
Figure 28B:
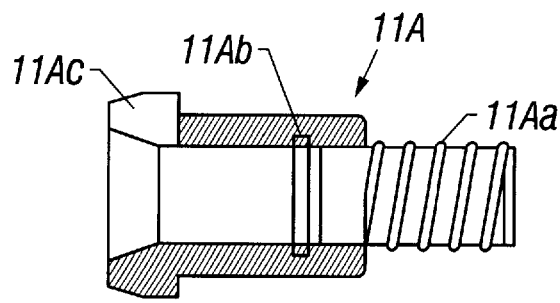
FIG. 28(b) is a front view of a partial section of the guide cylinder.
Figure 28C:
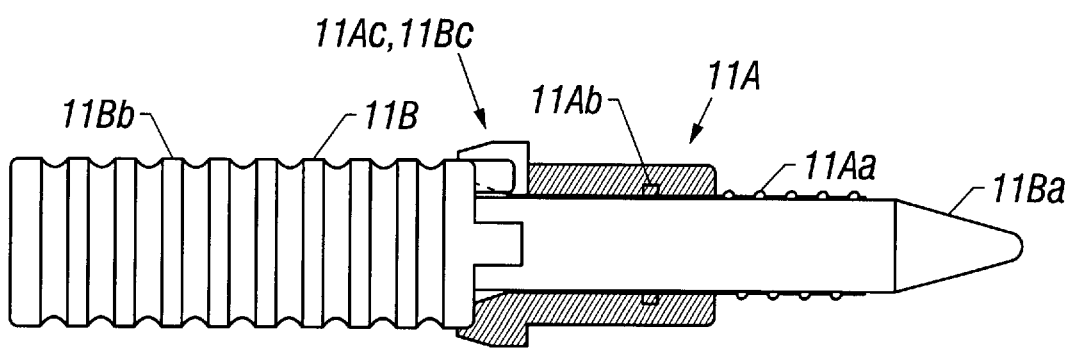
FIG. 28(c) is a front view of a partial section when the grip plug is incorporated in the guide cylinder.

FIG. 28(a) is a front view of the grip plug, FIG. 28(b) is a front view of a partial section of the guide cylinder, FIG. 28(c) is a front view of a partial section when the grip plug is incorporated in the guide cylinder, and FIG. 28(a) also shows the grip plug when seen from front.

The grip plug 11B isn't used in case of the guide cylinder of FIG. 10 and is inserted in the guide cylinder 11A. It is provided with a rounded point 11Ba at its point, a grip 11Bb at an end for easy holding. It is so designed to be easily operated by holding it when it is inserted in the guide cylinder 11A and to be easily inserted in the trocar site because of the rounded point 11Ba.

The guide cylinder 11A is designed so as to be inserted in the trocar site without difficulty because of a spiral 11Aa provided for its outer diameter comparing to the guide cylinder 11 of FIG. 10. An O-ring 11Ab for sealing is provided for its inner diameter so as to be kept airtight when the grip plug 11B is inserted.

A turn-stop concave 11Ac is provided for the brim provided at the entrance of the guide cylinder 11A and a turn-stop projection 11Bc provided at the tip of the grip 11Bb of the grip plug 11B is inserted in the concave 11Ac. The guide cylinder 11A inserted in the trocar site is turned together by means of the grip plug 11B inserted in the guide cylinder 11A. Accordingly the guide cylinder 11A can be inserted in the trocar site because of the operation of the spiral 11Aa without imposing a burden on the abdomen.

Figure 29A:
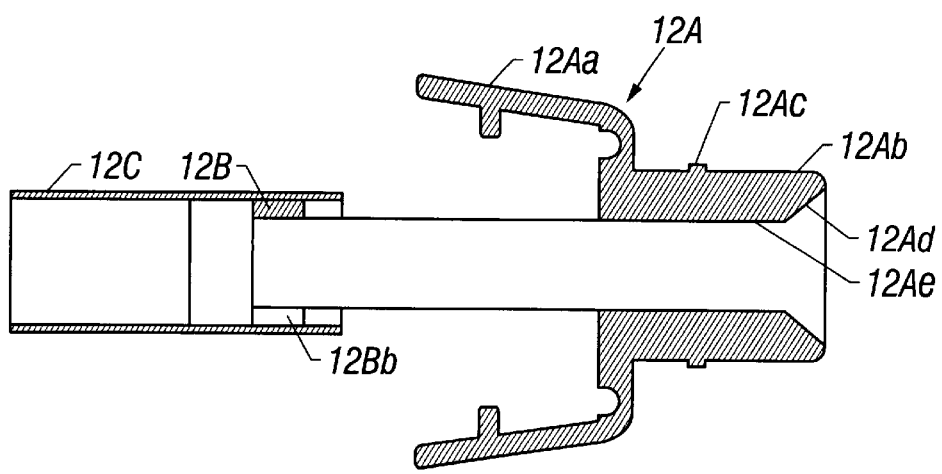
FIG. 29(*a*) shows a vertical sectional view when the push shaft having a pipe guide and the cap for folding are set.
Figure 29B:
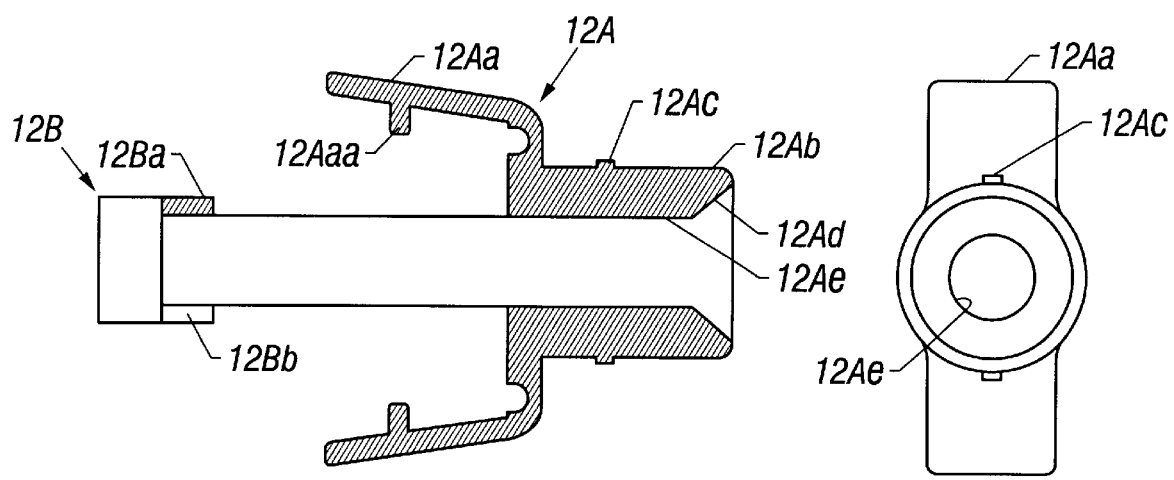
Figure 29C:
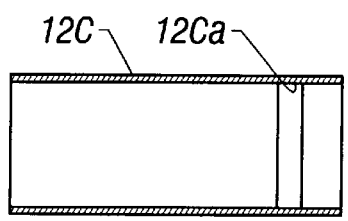

FIG. 29(a) shows a vertical sectional view when the push shaft having the pipe guide and the cap for folding are set. FIG. 29(b) is a vertical sectional view of the push shaft having the pipe guide, and FIG. 29(c) is a sectional view of the cap for folding. FIG. 29(b) also shows a view of the pipe guide when seen from the front.

The push shaft 12A of FIG. 29(b), the same as the tip of the push shaft 12 in FIG. 10, is provided with a pipe guide 12B at its tip end and at the other end a receiving cylinder 12Ab projecting a wing plate 12Aa having a small projection 12Aaa at both sides. The entrance of the receiving cylinder 12Ab is formed with a tapered female part 12Ad, the same as the tapered female part 12a of the push shaft 12. A guide projection 12Ac is provided at two positions of the outer circumference of the receiving cylinder 12Ab, those of which oppose each other on the circumference.

The pipe guide 12B is cylindrical and has a thick portion where the half length of the pipe guide 12B is attached with the tip end of the push shaft 12 and a male screw 12Ba is provided for the outer diameter of the thick part. An escape groove 12Bb for freely attaching the tube 9 of the endo-bag 1C and 1D is provided along the whole length of the cylinder including the male screw 12Ba.

The cap for folding 12C of FIG. 29(c) is a thin cylinder and is provided with a female screw 12Ca which is screwed into the male screw 12Ba of the pipe guide 12B at the inner diameter. The cap 12C is designed to cover the folded endo-bag 1C and 1D set at the tip end of the pipe guide 12B so as to keep the folding of the bag at its root. The cap 12C may be screwed until the connection is removed by screwing into the male screw of the pipe guide 12B and may be screwed back for this purpose. Otherwise, the cap 12C may be incorporated from the tip of the folded endo-bag 1C, 1D and may be used by screwing into the male screw 12Ba of the pipe guide 12B.

Figure 30A:
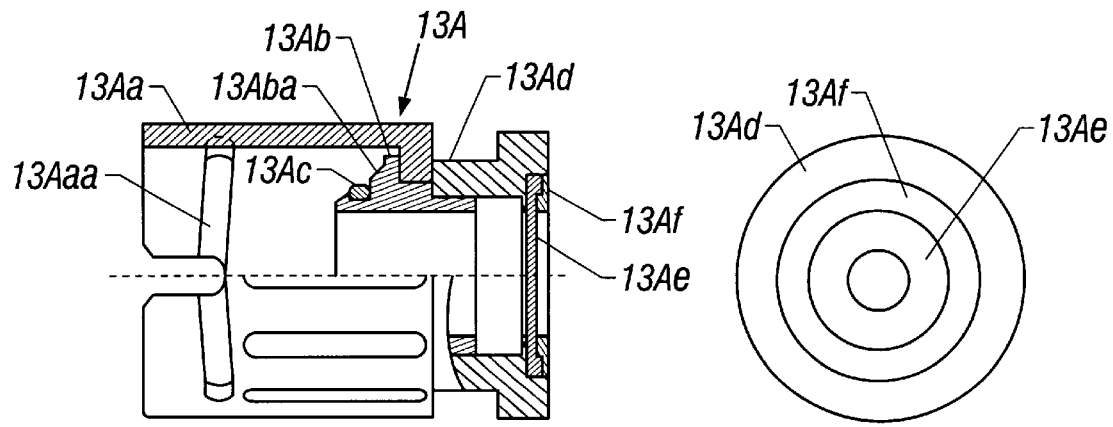
FIG. 30(*a*) is a front view of a partial section of the bag fixing cap.
Figure 30B:
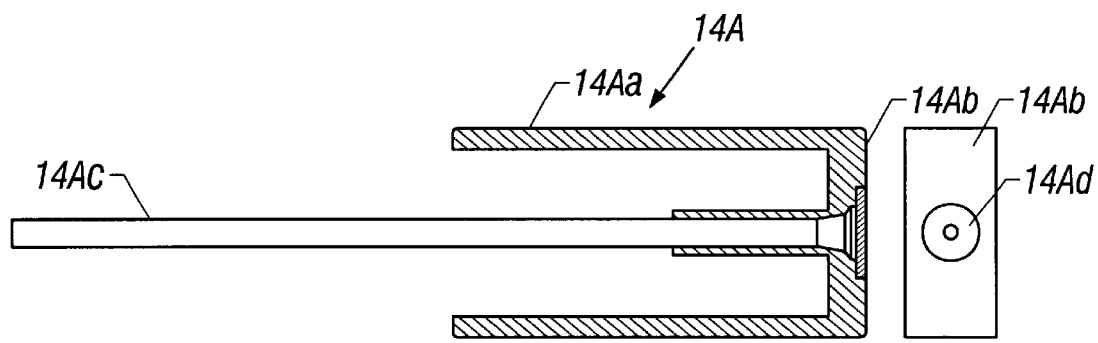

FIG. 30(a) is a front view of a partial section of the bag fixing cap, FIG. 30(b) is a vertical sectional view of the forceps guide. Each drawing also shows a view when seen from the side.

The bag fixing cap 13A of FIG. 30(a) has no sealing mechanism at the inner diameter of an inner body 13Ab provided with a tapered male part 13Aba comparing to the bag fixing cap 13. Instead, a sealing cap 13Ad having a sealing ring 13Ae is inserted outside at the entrance of the inner cap 13Ab. A push plate 13Af provided for the sealing cap 13Ad holds the sealing ring 13Ae. The inner diameter of the sealing ring 13Ae is set to keep airtight against the outer diameter of the pipe shaft 14Ac of the forceps guide 14A. The numeral 13Ac indicates an O-ring which is the same as the O-ring 13e of the bag fixing cap 13 of FIG. 10.

An outer cap 13Aa having a guide groove 13Aaa is the same as the outer cap 13a of the bag fixing cap 13 in FIG. 10. The guide projection 12Ac of the push shaft 12A is designed to be inserted in the guide groove 13Aaa of the outer cap 13Aa.

The forceps guide 14A of FIG. 30(b) is comprised of a brim 14Aa, a bottom 14Ab, and a pipe shaft 14Ac like the forceps guide 14 of FIG. 10 and has the same function such as the forceps guide 14.

FIG. 31(a)–FIG. 34(f) explain the procedure for containing the endo-bag into the inserting means for the endo-bag. Those figures correspond to FIG. 14(a) to FIG. 16(e) and only the difference will be explained. In the procedure, the endo-bag iC is used, however, the endo-bag ID can be used in the similar manner.

Figure 31A:
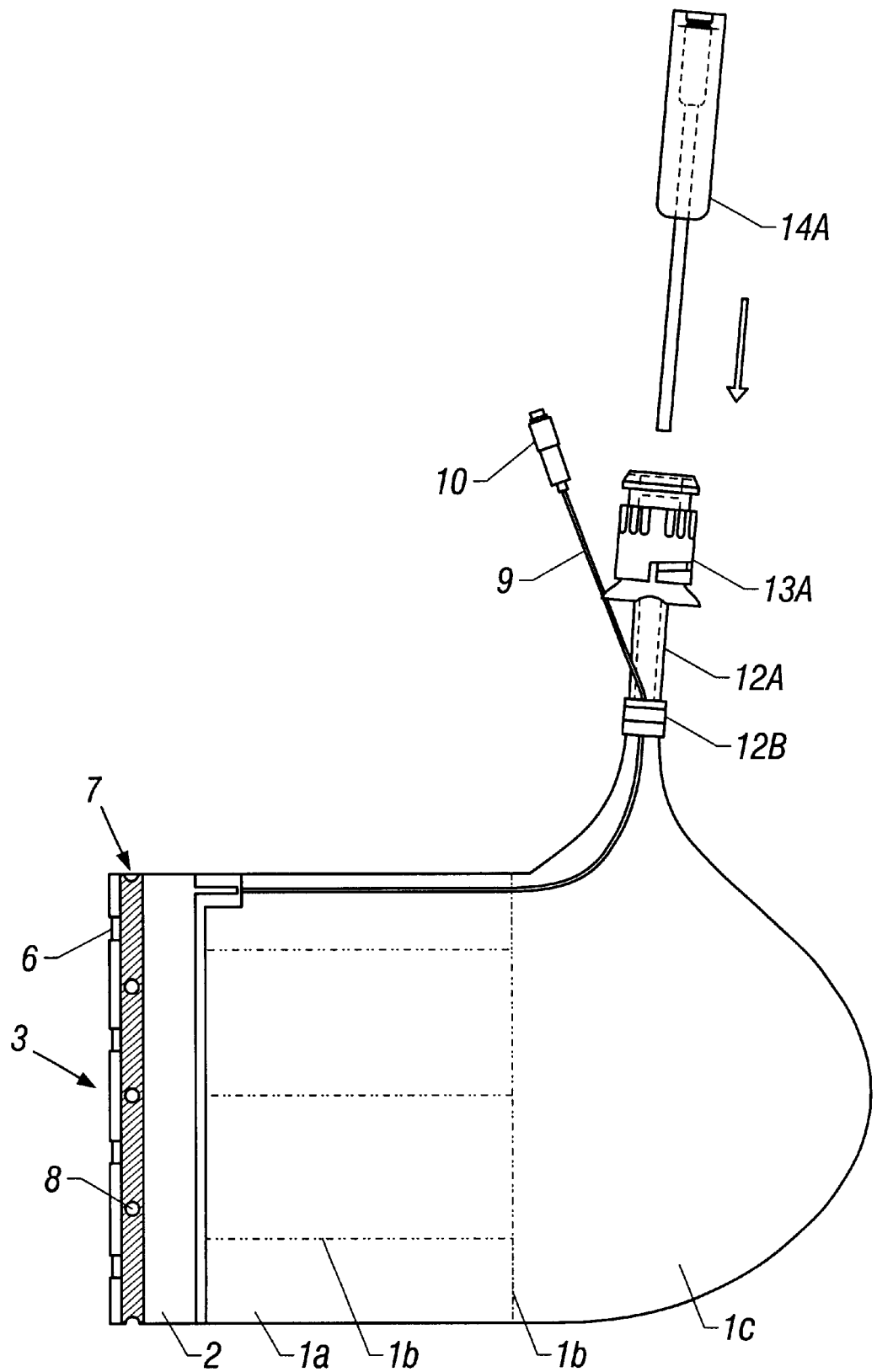
FIG. 31(*a*) shows when the inserting portion for surgical instrument of the endo-bag is set at the push shaft and the bag fixing cap and the forceps guide is inserted.

As shown in FIG. 31(a), the pipe guide 12B is inserted outside the neck of the outer circumference of the inserting portion for a surgical instrument 4 of the endo-bag 1C so as to insert the tube 9 into the escape groove 12Bb of the pipe guide 12B. The push shaft 12A is inserted in the inserting portion for a surgical instrument 4, the edge part of the inserting portion 4 is turned down, and the bag fixing cap 13A is covered on the turned-down portion. Because of its sealing mechanism, the push shaft 12A, the bag fixing cap 13A, and the inserting portion for a surgical instrument 4 can be sealed.

The tube 9 is supported to be positioned near the tip end of the push shaft 12A by the pipe guide 12B as shown in the figure. Under such a condition, the forceps guide 14A is inserted in the bag fixing cap 13A.

Figure 32B:
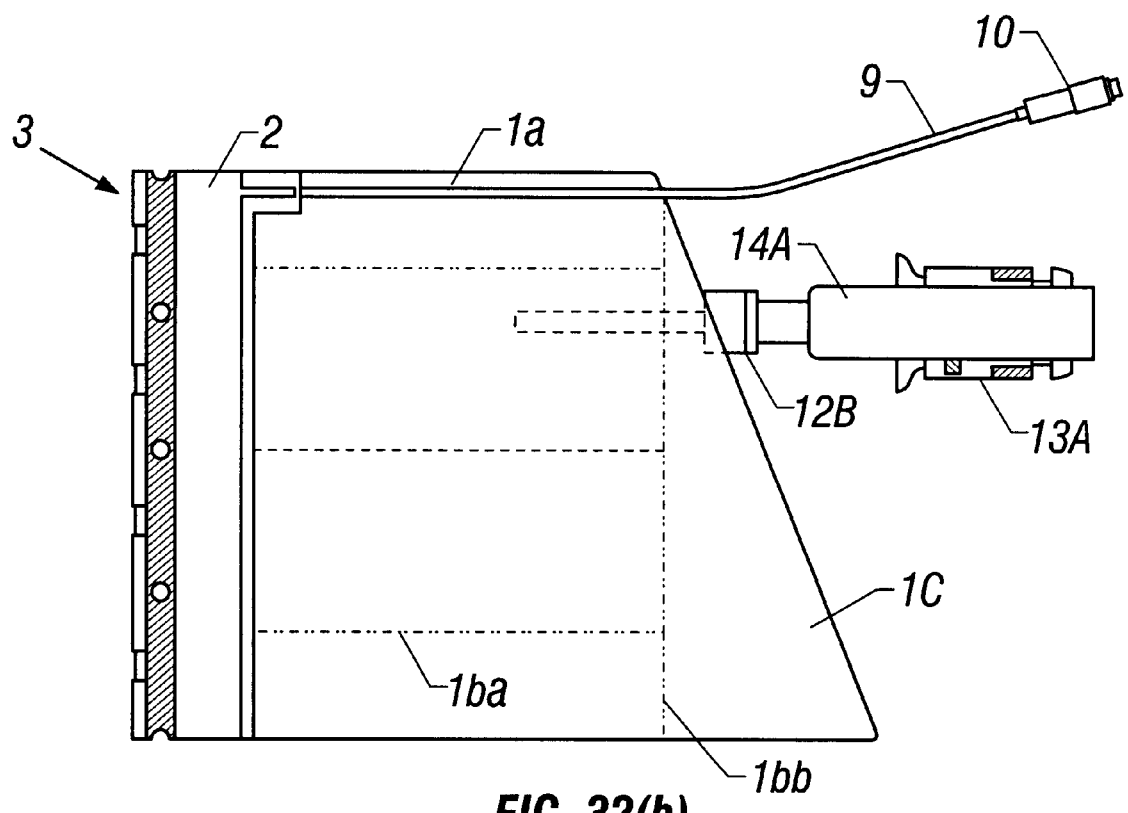
FIGS. 32(*b*) and 32(*c*) show the procedure the endo-bag is folded.
Figure 32C:
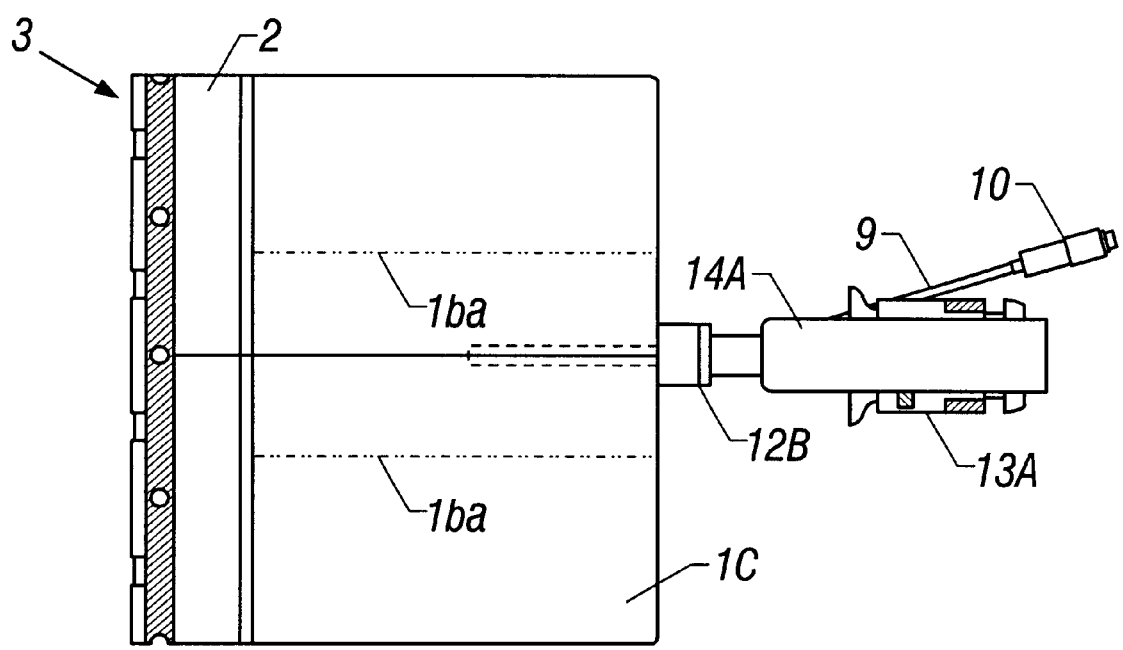

The rear part of the bag along a folding line 1bb is folded so as to be included in the inside of the receptacle portion 1a while keeping the direction of the inserting portion for a surgical instrument 4, the push shaft 12A set for the instrument 4, the bag fixing cap 13A, and the forceps 14A so as to be perpendicular to the front edge of the organ receiving mouth 3 of the endo-bag 1C as shown in FIG. 32(*b*).

Accordingly the rear part of the bag 1*a* along the line 1*bb* is completely folded into the receptacle portion 1*a* which is a front part along the line 1*bb* as shown in FIG. 32(*c*). FIG. 32(*c*) is a view when FIG. 32(*b*) is seen from the top and the bag is folded up to be flat when seen from the top.

The endo-bag 1C is formed with folding lines 1*b* as an aim of folding, so it can be folded easily. When the folding lines 1*b* are formed so as to fold the bag most appropriately based of experiences, the endo-bag 1C can be folded up into an ideal state.

Figure 33D:
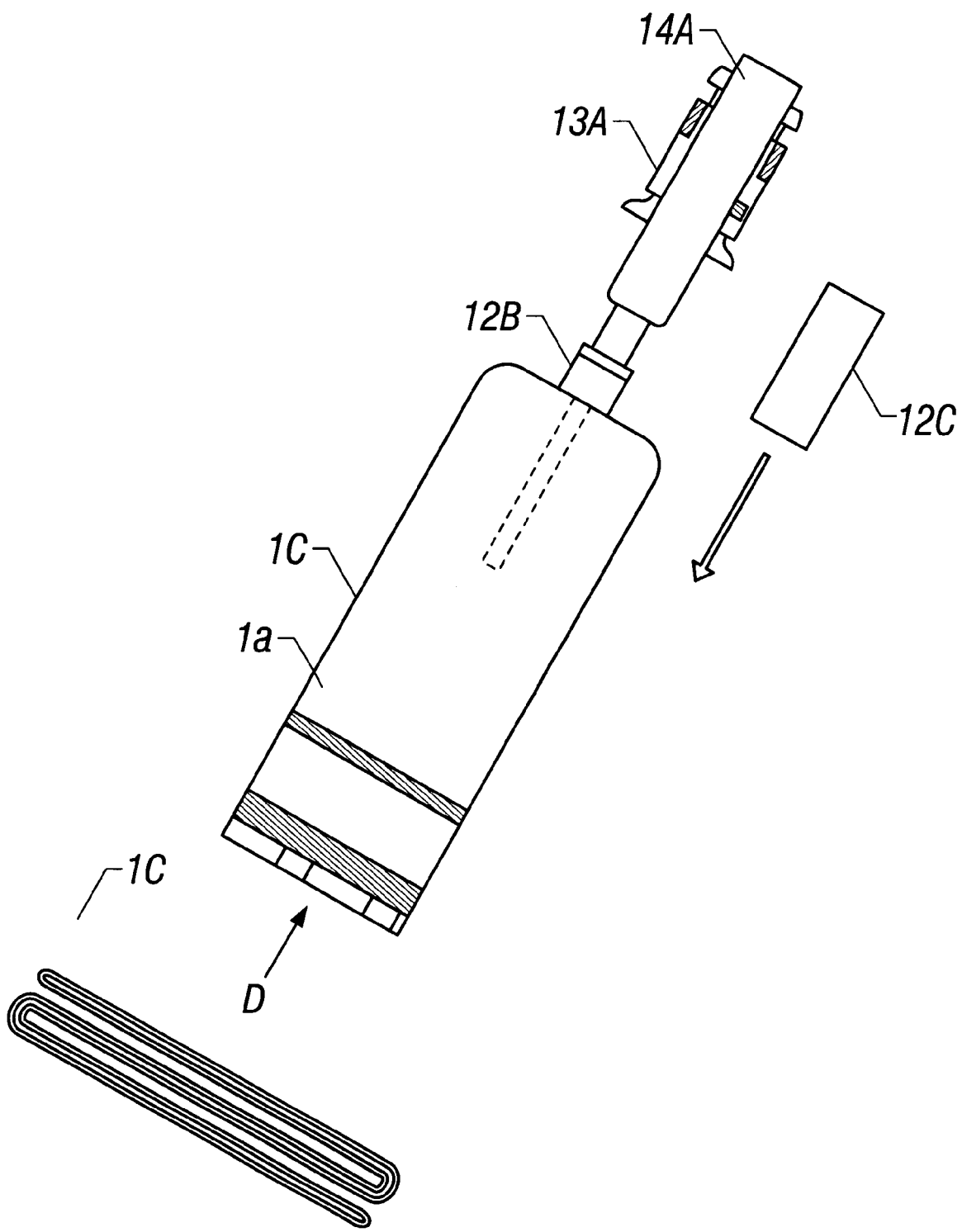
FIG. 33(*d*) shows the endo-bag is folded into three layer.

As shown in FIG. 33(*d*), the bag 1*a* which is folded in FIG. 32(*c*) is further folded at triplicate along the lines 1*ba*. FIG. 33 shows also a perspective view seen from D of the triplicately folded bag.

The folded bag 1*a* of the endo-bag 1C is further folded and inserted into the guide cylinder 11A, explained hereinafter, by means of the cap for folding 12C.

Figure 34E:
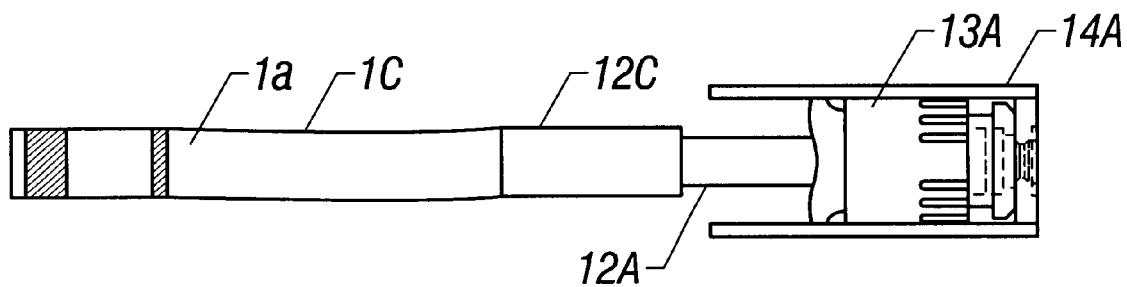
FIG. 34(*e*) is a front view when the endo-bag is further folded and set by means of the cap for folding and FIG. 34(*f*) shows its plan view.
Figure 34F:
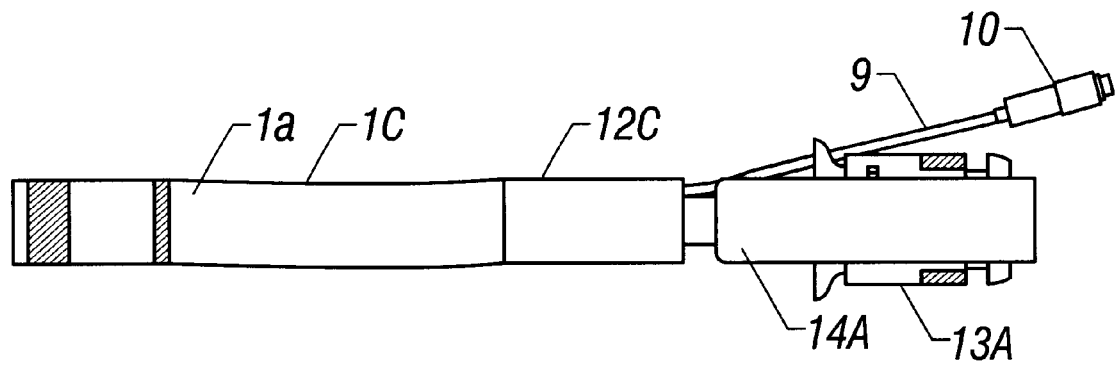

FIG. 34(*e*) is a front view of the folded endo-bag 1C when the push shaft 12A, the bag fixing cap 13A, and the forceps guide 14A are set. FIG. 34(*f*) shows its plan view.

Figure 35G:
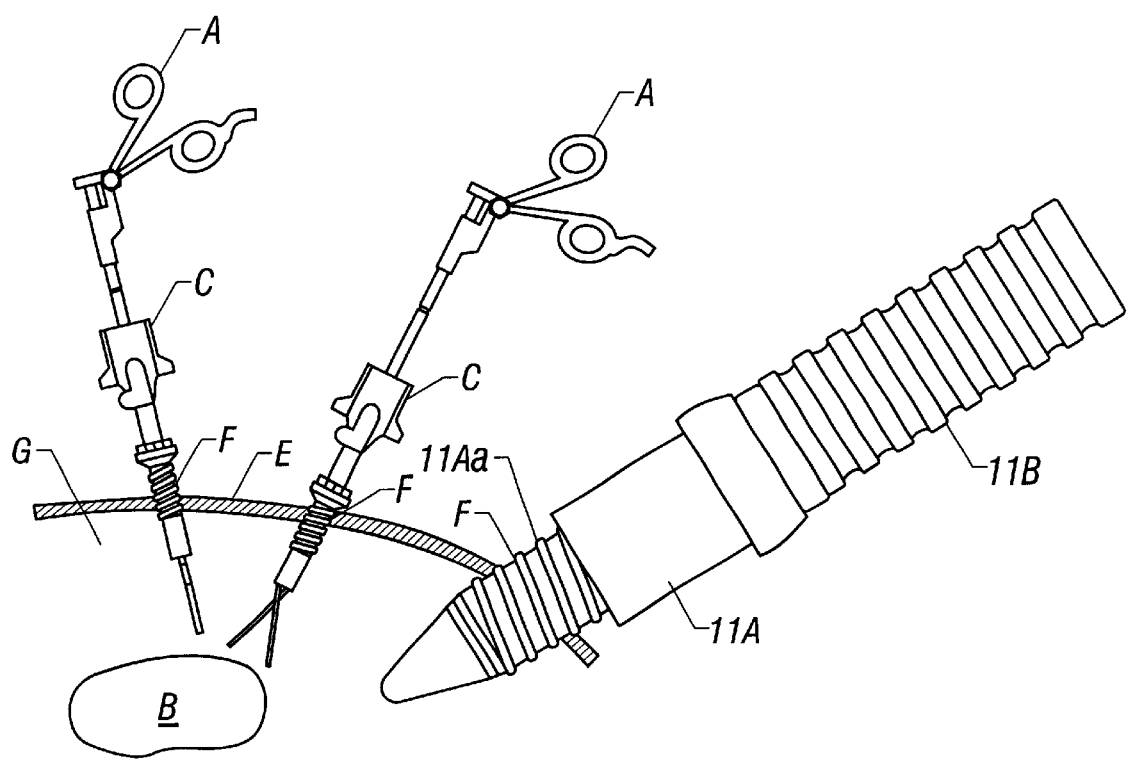
FIG. 35(*g*) shows when the guide cylinder incorporated with the grip plug is inserted in the trocar puncture.
Figure 38K:
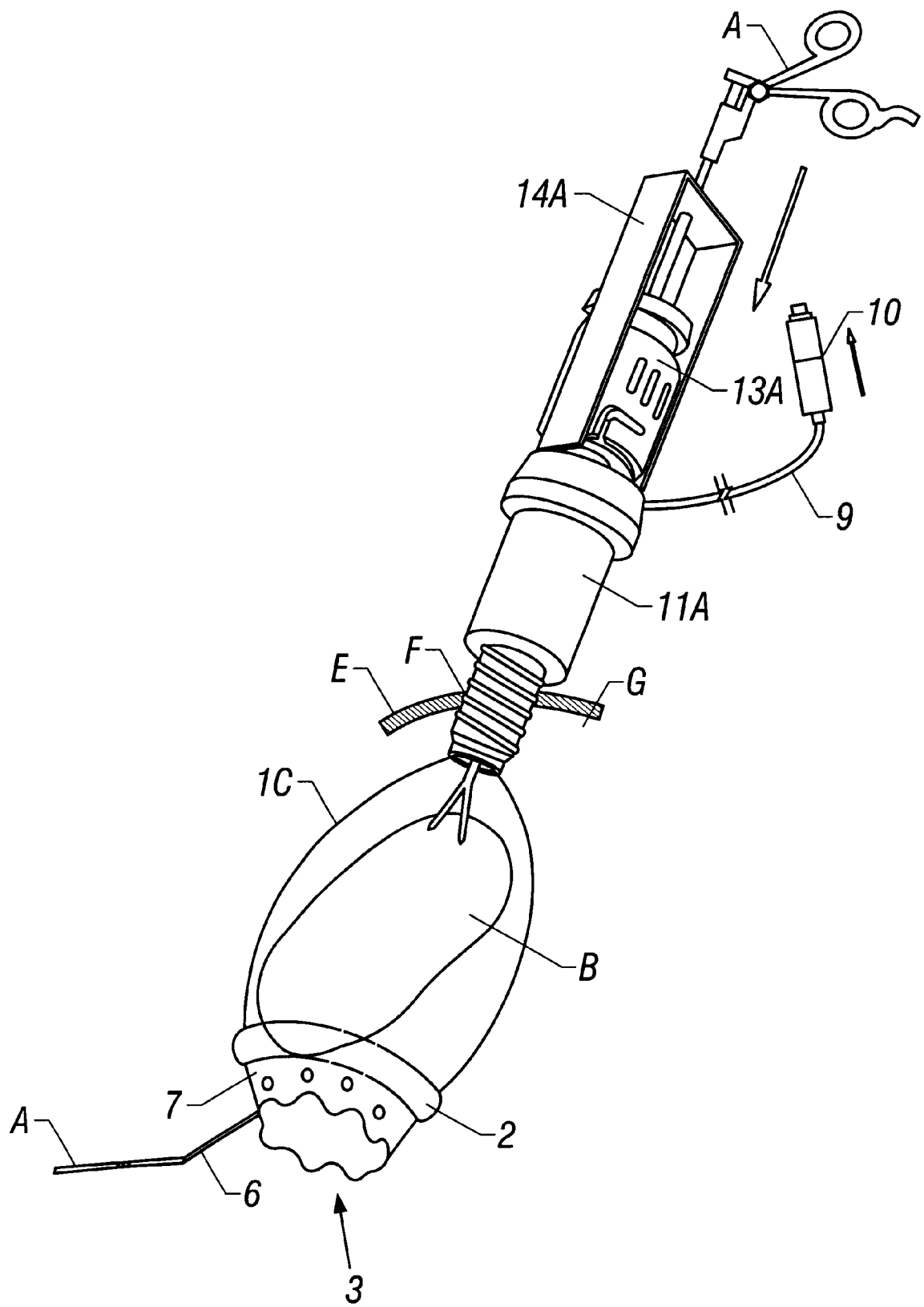
Figure 39A:
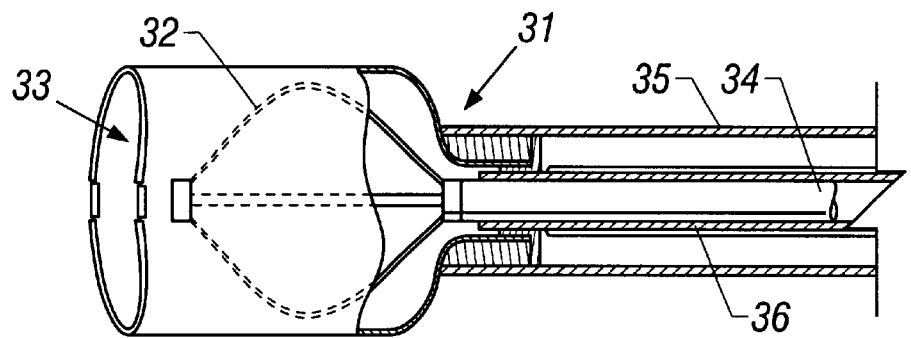
FIGS. 39(*a*), 39(*b*), 39(*c*) shows the endo-bag of the prior art.
Figure 39B:
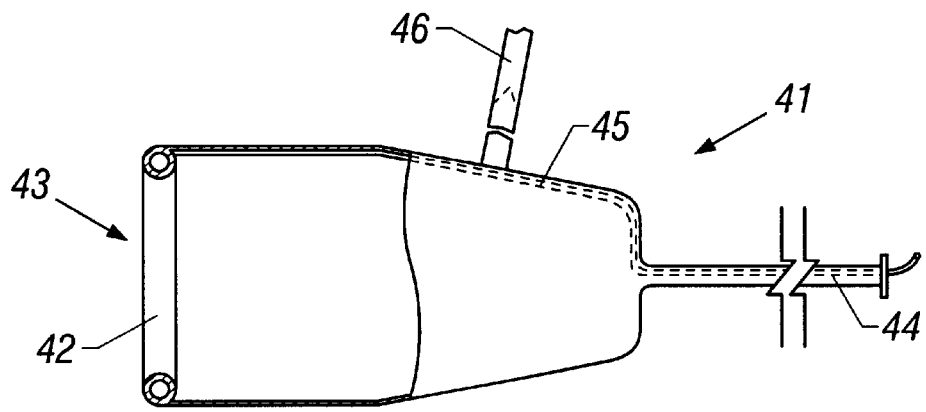
Figure 39C:
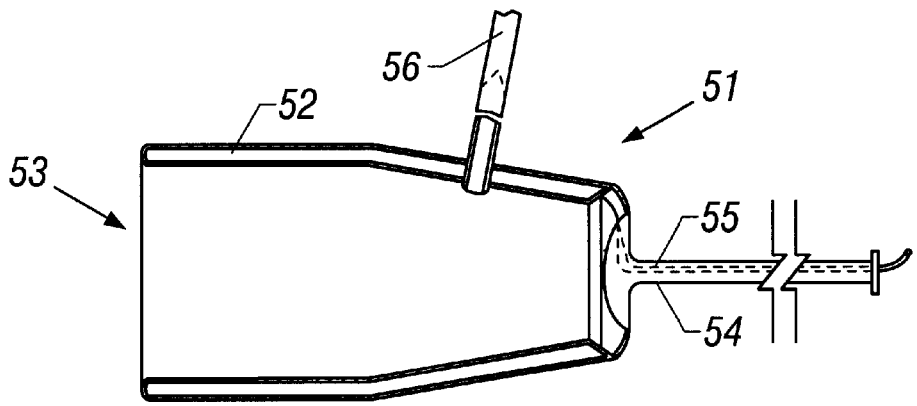

FIG. 35(*g*)–FIG. 38(*k*) show the procedure when the above-mentioned endo-bag 1C is inserted in the abdominal cavity and the removed organ is contained therein. They correspond to FIG. 17(*f*) to FIG. 20(*j*) and FIG. 1 and only the difference will be explained.

As shown in FIG. 35(*g*), the guide cylinder 11A which is inserted with the grip plug 11B so as to prevent entering of the outside air is held by the grip of the grip plug 11B and is inserted into the trocar site F instead of the trocar C.

The contacting part of the guide cylinder 11A on the trocar site F isn't straight, unlike the guide cylinder 11 of FIG. 18, and is formed as spiral 11A*a* like a usual trocar. Accordingly, the guide cylinder 11A doesn't apply extra pressure on the abdominal wall E by rotating to be inserted into the trocar site F. Further, it is prevented from entering the outside air by means of the grip plug 11B. The grip plug 11B can be operated effectively when inserted in the trocar site F because it is turned together with the guide cylinder 11A by the operation of turn-stop parts 11A*c* and 11B*c*.

Figure 36H:
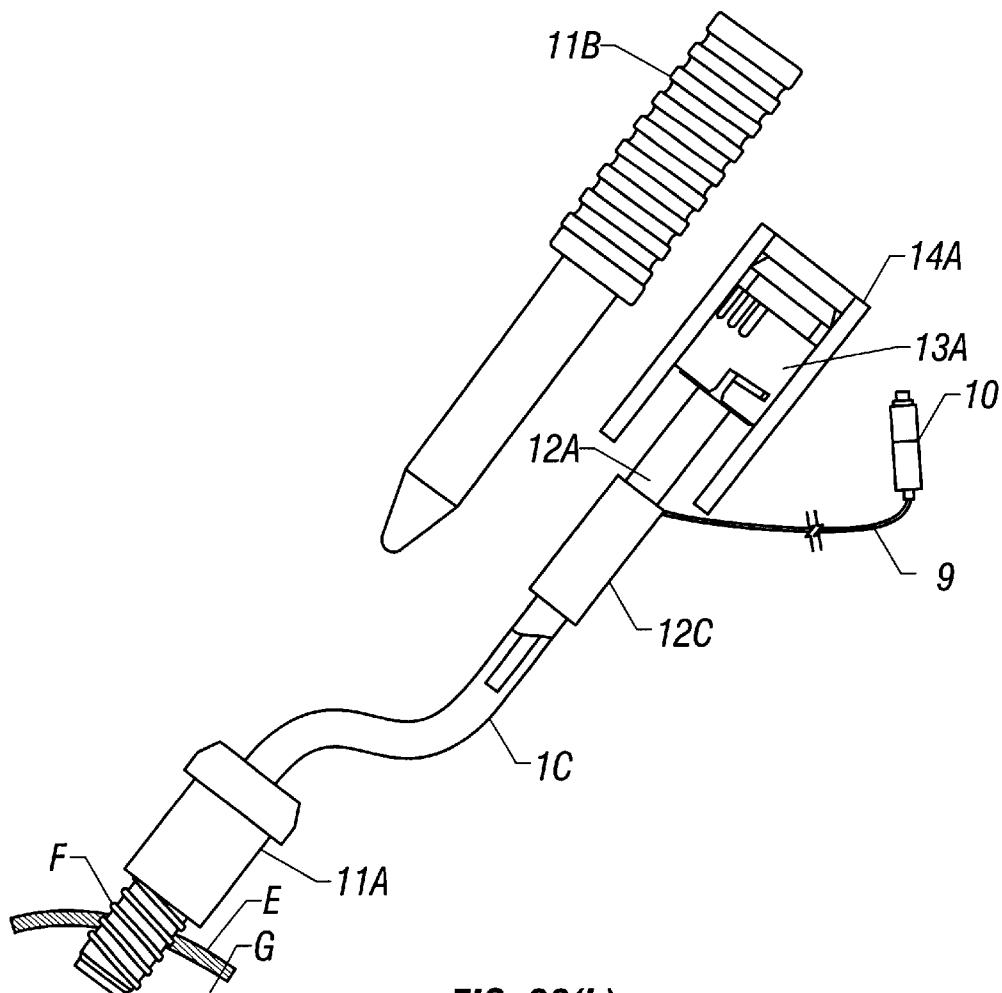
FIG. 36(*h*) shows when the folded endo-bag is inserted by removing the grip plug, and FIG. 36(*i*) shows when the endo-bag is inserted in the abdominal cavity by means of the forceps guide.
Figure 36I:
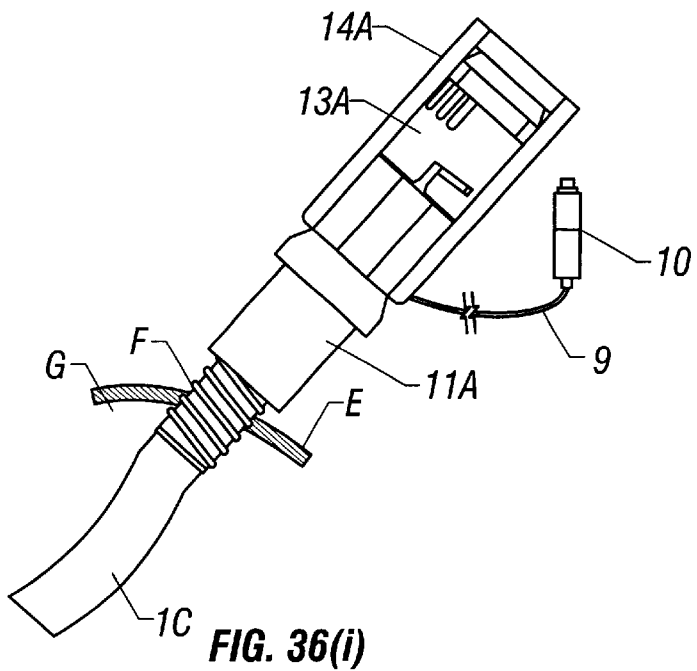

When the guide cylinder 11A is inserted into a fixed portion and the endo-bag 1C is prepared, the grip plug 11B is removed and the prepared endo-bag 1 is quickly inserted in the guide cylinder 11A as shown in FIG.36(*h*).

Figure 37J:
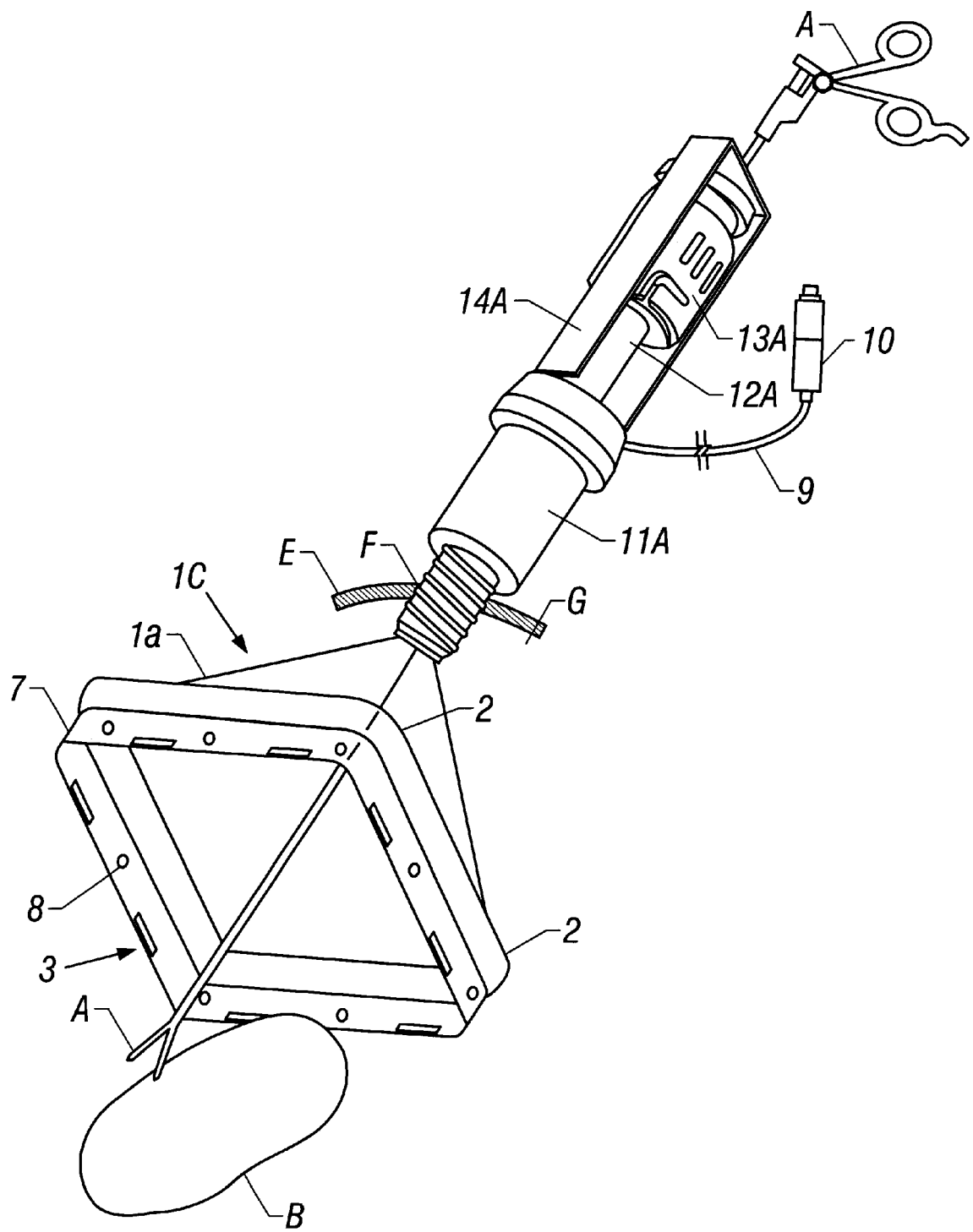
FIG. 37(*j*) shows when the removed organ is contained by expanding the endo-bag.

Then, the forceps guide 14A is pushed, the receptacle portion 1*a* of the endo-bag 1C folded in the cap for folding 12C is pushed out and inserted in the abdominal cavity G as shown in FIG. 36(*i*). When a fluid, clean water in this embodiment, is pumped into the inflation-type frame edge 2 from the check valve 10, the inflation-type frame edge 2 is expanded into quadrangular along the abdominal wall E with a little amount of fluid and less fluid pressure as shown in FIG. 37(*j*). The removed organ B can be easily taken in the receptacle portion 1*a* of the endo-bag 1C by operating the forceps A through the opening provided for the forceps guide 14A.

As shown in FIG. 38(*k*), the remainder of the endo-bag 1C folded in the cap for folding 12C is pushed out by pushing the bag fixing cap 13A and the push shaft 12A after the removed organ B is contained in the endo-bag 1C. Then the closing string 6 provided for the closing margin 7 of the endo-bag 1C is pulled up by inserting the forceps 4 from another trocar C so as to close the organ receiving mouth 3.

The procedures after that are the same as the procedures explained referring to FIG. 21 (*k*)–FIG. 25(*o*). The endo-bag 1C containing the removed organ B can be taken out of the abdominal cavity G.

According to the endo-bag and the inserting means for the endo-bag of the present invention, the endo-bag can be inserted into the abdominal cavity easily and safely. The organ receiving mouth can be easily and safely expanded with less pressure and less amount of fluid. The endo-bag is suitable for the endoscopic surgery because it is hard to be deformed and quickly takes the removed organ therein. Moreover, the endo-bag can be easily folded, contained and treated. Furthermore, the removed organ can be taken out of the patient's body safely and quickly because the endo-bag imposes less burden on the patient's body and is less affected by the outside air.

What is claimed is:

1. An endo-bag with an inflation-type receiving mouth, comprising a flexible bag body having an organ receiving mouth provided with an inflation-type frame edge and an inserting portion for a surgical instrument, said inflation-type frame edge being provided with a plurality of gores formed by three-dimensional tailoring and being so constructed as to be inflated and expanded to open said organ receiving mouth by pumping a fluid therein.

2. An endo-bag according to claim 1, wherein said inflation-type frame edge has corners with joints of gores formed on an inside thereof.

3. An endo-bag according to claim 1, wherein said inflation-type frame edge is such constructed that a surface of said edge inflates almost uniformly by pumping a fluid therein.

4. An endo-bag according to claim 1, wherein said inflation-type frame edge has corners with gores made in a shape of bellows.

5. An endo-bag according to claim 1, wherein said inflation-type frame edge has corners shaped as arc-like form.

6. An endo-bag according to claim 1, wherein said inflation type frame edge is made of a low-pliable sheet material.

7. An endo-bag according to claim 1, wherein said organ receiving mouth is provided with a closing margin which has therearound a plurality of through holes with a closing string put through said holes.

8. An endo-bag according to claim 7, wherein said closing margin is provided with a catching hole.

9. An endo-bag according to claim 8, wherein said closing string is formed as ring shape without knot nor end.

10. An endo-bag according to claim 7, wherein said closing string is formed as ring shape without knot nor end.

11. An endo-bag according to claim 1, wherein said inserting portion for a surgical instruments is provided on the opposite side of said organ receiving mouth.

12. An endo-bag according to claim 11, wherein said bag further comprises on a surrounding wall of said bag body a plurality of inflation-type rib frames running from said organ receiving mouth toward said inserting portion for a surgical instrument and communicating with said inflation-type frame edge.

13. An endo-bag according to claim 1, wherein said bag body is made of a 50~80-micron-thick strong and flexible urethane sheet or polyethylene sheet.

14. An endo-bag according to claim 1, wherein said bag body is made of a transparent or semi-transparent urethane sheet or polyethylene sheet.

15. An endo-bag according to claim 1, wherein a receptacle portion of said bag body is constructed from at least one sheet.

16. An endo-bag according to claim 1, wherein clean air, carbonic acid gas or sterilized distilled water is pumped into said inflation-type frame edge as said fluid.

17. An endo-bag with an inflation-type receiving mouth, comprising a flexible bag body having an organ receiving mouth provided with an inflation-type frame edge and an inserting portion for a surgical instrument, said inflation-type frame edge being so constructed as to be inflated and expanded in a polygonal form to open said organ receiving mouth by pumping a fluid therein.

18. An endo-bag according to claim 17, wherein said inflation-type frame edge is formed in a polygonal shape and is provided with gores on an outer circumference of said frame edge at appropriate intervals so as to form corners of a polygonal shape by pumping a fluid therein.

19. An endo-bag according to claim 18, wherein said inflation-type frame edge has corners with joints of gores formed on an inside thereof.

20. An endo-bag according to claim 18, herein said inflation-type frame edge is formed as a triangular, quadrangular or pentagonal shape.

21. An endo-bag according to claim 18, wherein said inflation-type frame edge is such constructed that a surface of said edge inflates almost uniformly by pumping a fluid therein.

22. An endo-bag according to claim 18, wherein said inflation-type frame edge has corners with gores made in a shape of bellows.

23. An endo-bag according to claim 18, wherein said inflation-type frame edge has a plurality of inflation-type cylindrical elements communicating with each other.

24. An endo-bag according to claim 18, wherein said inflation-type frame edge has corners shaped as arc-like form.

25. An endo-bag according to claim 18, wherein said inflation type frame edge is made of a low-pliable sheet material.

26. An endo-bag according to claim 18, wherein said organ receiving mouth is provided with a closing margin which has therearound a plurality of through holes with a closing string put through said holes.

27. An endo-bag according to claim 26, wherein said closing margin is provided with a catching hole.

28. An endo-bag according to claim 27, wherein said closing string is formed as ring shape without knot nor end.

29. An endo-bag according to claim 26, wherein said closing string is formed as ring shape without knot nor end.

30. An endo-bag according to claim 18, wherein said inserting portion for a surgical instruments is provided on an opposite side of said organ receiving mouth.

31. An endo-bag according to claim 30, wherein said bag further comprises on a surrounding wall of said bag body a plurality of inflation-type rib frames running from said organ receiving mouth toward said inserting portion for a surgical instrument and communicating with said inflation-type frame edge.

32. An endo-bag according to claim 18, wherein said bag body is made of a 50~80-micron-thick strong and flexible urethane sheet or polyethylene sheet.

33. An endo-bag according to claim 18, wherein said bag body is made of a transparent or semi-transparent urethane sheet or polyethylene sheet.

34. An endo-bag according to claim 18, wherein a receptacle portion of said bag body is constructed from at least one sheet.

35. An endo-bag according to claim 18, wherein clean air, carbonic acid gas or sterilized distilled water is pumped into said inflation-type frame edge as said fluid.

36. An endo-bag according to claim 18, wherein said inserting portion for a surgical instruments has an instrument receiving member with an insertion hole to allow said surgical instrument to pass therethrough and a sealing plug to airtightly close said insertion hole as necessary.

37. An endo-bag with an inflation-type receiving mouth, comprising a flexible bag body having an organ receiving mouth provided with an inflation-type frame edge and an inserting portion for a surgical instrument, said inflation-type frame edge being so constructed as to be formed in a circular or polygonal shape made of series of plural segments expanded by pumping a fluid therein.

38. An endo-bag according to claim 37, wherein said inserting portion for a surgical instrument has an instrument receiving member with an insertion hole to allow said surgical instrument to pass therethrough and said insertion hole is sealed with a sealing plug.

39. The combination of an instrument for inserting an endo-bag into an abdominal cavity and an endo-bag, said combination comprising:

a guide cylindrical body to be inserted into the abdominal cavity, said cylindrical body containing a folded endo-bag, said folded endo-bag comprising a flexible bag body having an organ receiving mouth provided with an inflation-type frame edge and an inserting portion for a surgical instrument, said inflation-type frame edge being provided with a plurality of gores formed by three-dimensional tailoring and being so constructed as to be inflated and expanded to open said organ receiving mouth by pumping a fluid therein; and a push shaft for inserting said endo-bag which is folded into said guide cylindrical body into the abdominal cavity.

40. The combination as defined in claim 39, wherein said guide cylindrical body is provided with a sealing means to seal the ends of said inserting portion for a surgical instrument, and said push shaft is provided with an insertion hole so as to allow air-tight insertion of the surgical instrument into said endo-bag.

41. The combination of an instrument for inserting an endo-bag into an abdominal cavity and an endo-bag, said combination comprising:

a guide cylindrical body to be inserted into the abdominal cavity, said cylindrical body containing a folded endo-bag, said folded endo-bag comprising a flexible bag body having an organ receiving mouth provided with an inflation-type frame edge and an inserting portion for a surgical instrument, said inflation-type frame edge being provided with a plurality of gores formed by three-dimensional tailoring and being so constructed as to be inflated and expanded to open said organ receiving mouth by pumping a fluid therein, wherein said inserting portion for a surgical instrument has an instrument receiving member with an insertion hole for allowing said surgical instrument to pass therethrough, said insertion hole being sealed with a sealing plug; and a push shaft for inserting said endo-bag which is folded into said guide cylindrical body into the abdominal cavity; and wherein said push shaft is provided with a fitting hole so constructed as to allow said instrument receiving member to pass through when said instrument receiving member conforms to said fitting hole.

* * * * *